United States Patent
Seul et al.

(10) Patent No.: US 8,615,367 B2
(45) Date of Patent: Dec. 24, 2013

(54) NUMBER CODING FOR IDENTIFICATION OF SUBTYPES OF CODED TYPES OF SOLID PHASE CARRIERS

(75) Inventors: Michael Seul, Fanwood, NJ (US); Chiu Wo Chau, Edison, NJ (US); Enqing Tan, Kendall Park, NJ (US)

(73) Assignee: Bioarray Solutions, Ltd., Warren, NJ (US)

( * ) Notice: Subject to any disclaimer, the term of this patent is extended or adjusted under 35 U.S.C. 154(b) by 0 days.

(21) Appl. No.: 13/071,055

(22) Filed: Mar. 24, 2011

(65) Prior Publication Data

US 2011/0184655 A1 Jul. 28, 2011

Related U.S. Application Data

(62) Division of application No. 10/943,760, filed on Sep. 17, 2004, now Pat. No. 7,927,796.

(60) Provisional application No. 60/504,294, filed on Sep. 18, 2003.

(51) Int. Cl.
| | |
|---|---|
| G01N 33/48 | (2006.01) |
| G01N 31/00 | (2006.01) |
| G06G 7/48 | (2006.01) |
| G06G 7/58 | (2006.01) |

(52) U.S. Cl.
USPC .................. 702/19; 702/22; 703/11; 703/12

(58) Field of Classification Search
None
See application file for complete search history.

(56) References Cited

U.S. PATENT DOCUMENTS

| | | | |
|---|---|---|---|
| 3,329,638 | A | 7/1967 | Blyth |
| 3,574,614 | A | 4/1971 | Carreira |
| 3,790,492 | A | 2/1974 | Fulwyler |
| 3,957,741 | A | 5/1976 | Rembaum et al. |
| 3,982,182 | A | 9/1976 | Hogg |

(Continued)

FOREIGN PATENT DOCUMENTS

| | | |
|---|---|---|
| CA | 1248873 | 1/1989 |
| DE | 4035714 | 5/1992 |

(Continued)

OTHER PUBLICATIONS

Braeckmans et al., "Encoding microcarriers by spatial selective photobleaching", 2003, Nature materials, vol. 2, No. 3, pp. 169-173.*

(Continued)

*Primary Examiner* — Larry D Riggs, II
(74) *Attorney, Agent, or Firm* — Womble Carlyle Sandridge & Rice, LLP

(57) ABSTRACT

Disclosed is number coding of pairs ("doublets") or small sets ("multiplets") of solid phase carriers which provides distinguishable subtypes of a given type of such carriers, where each carrier type is distinguishable on the bases of a different code. Such number coding is useful for augmenting a coding system, such as a color code, and thereby effectively multiplying the number of "colors" (distinguishable sub-types). It can be applied, for example, to determine whether a sample is homozygous or heterozygous at a number of different sites for one of two different alleles, where the same color code is applied for each of the two alleles, and the alleles with the same color code are distinguished by knowing how many carriers are associated with molecules which detect each different allele.

8 Claims, 12 Drawing Sheets

(56) References Cited

U.S. PATENT DOCUMENTS

| | | |
|---|---|---|
| 3,989,775 A | 11/1976 | Jack et al. |
| 3,998,525 A | 12/1976 | Giglia |
| 4,003,713 A | 1/1977 | Bowser |
| 4,046,667 A | 9/1977 | Goetz |
| 4,055,799 A | 10/1977 | Coster et al. |
| 4,075,013 A | 2/1978 | Ward et al. |
| 4,102,990 A | 7/1978 | Uzgiris |
| 4,140,937 A | 2/1979 | Vecht et al. |
| 4,143,203 A | 3/1979 | Rigopulos et al. |
| 4,199,363 A | 4/1980 | Chen |
| 4,258,001 A | 3/1981 | Pierce et al. |
| 4,267,235 A | 5/1981 | Rembaum et al. |
| 4,275,053 A | 6/1981 | Rosenfield et al. |
| 4,326,008 A | 4/1982 | Rembaum |
| 4,336,173 A | 6/1982 | Ugelstad |
| 4,339,337 A | 7/1982 | Tricot et al. |
| 4,358,388 A | 11/1982 | Daniel et al. |
| 4,383,529 A | 5/1983 | Webster |
| 4,421,896 A | 12/1983 | Dorman |
| 4,456,513 A | 6/1984 | Kawai et al. |
| 4,459,378 A | 7/1984 | Ugelstad |
| 4,487,855 A | 12/1984 | Shih et al. |
| 4,497,208 A | 2/1985 | Oja et al. |
| 4,499,052 A | 2/1985 | Fulwyler |
| 4,575,407 A | 3/1986 | Diller |
| 4,591,550 A | 5/1986 | Hafeman et al. |
| 4,602,989 A | 7/1986 | Culkin |
| 4,613,559 A | 9/1986 | Ober et al. |
| 4,647,544 A | 3/1987 | Nicoli et al. |
| 4,654,267 A | 3/1987 | Ugelstad et al. |
| 4,663,408 A | 5/1987 | Schulz et al. |
| 4,665,020 A | 5/1987 | Saunders |
| 4,672,040 A | 6/1987 | Josephson |
| 4,679,439 A | 7/1987 | Culkin |
| 4,680,332 A | 7/1987 | Hair et al. |
| 4,702,598 A | 10/1987 | Böhmer |
| 4,717,655 A | 1/1988 | Fulwyler |
| 4,753,775 A | 6/1988 | Ebersole et al. |
| 4,774,189 A | 9/1988 | Schwartz |
| 4,774,265 A | 9/1988 | Ugelstad et al. |
| 4,791,310 A | 12/1988 | Honig et al. |
| 4,795,698 A | 1/1989 | Owen et al. |
| 4,806,313 A | 2/1989 | Ebersole et al. |
| 4,806,776 A | 2/1989 | Kley |
| 4,822,746 A | 4/1989 | Walt |
| 4,824,941 A | 4/1989 | Gordon et al. |
| 4,829,101 A | 5/1989 | Kraemer et al. |
| 4,832,814 A | 5/1989 | Root |
| 4,851,331 A | 7/1989 | Vary et al. |
| 4,873,102 A | 10/1989 | Chang et al. |
| 4,891,324 A | 1/1990 | Pease et al. |
| 4,911,806 A | 3/1990 | Hofmann |
| 4,920,056 A | 4/1990 | Dasgupta |
| 4,994,373 A | 2/1991 | Stavrianopoulos et al. |
| 4,996,265 A | 2/1991 | Okubo et al. |
| 5,002,867 A | 3/1991 | Macevicz |
| 5,015,452 A | 5/1991 | Matijevic |
| 5,028,545 A | 7/1991 | Soini |
| 5,073,498 A | 12/1991 | Schwartz et al. |
| 5,075,217 A | 12/1991 | Weber |
| 5,091,206 A | 2/1992 | Wang et al. |
| 5,105,305 A | 4/1992 | Betzig et al. |
| 5,114,864 A | 5/1992 | Walt |
| 5,126,239 A | 6/1992 | Livak et al. |
| 5,128,006 A | 7/1992 | Mitchell et al. |
| 5,132,097 A | 7/1992 | Van Deusen et al. |
| 5,132,242 A | 7/1992 | Cheung |
| 5,143,853 A | 9/1992 | Walt |
| 5,143,854 A | 9/1992 | Pirrung et al. |
| 5,147,777 A | 9/1992 | Sutton et al. |
| 5,155,044 A | 10/1992 | Ledis et al. |
| 5,173,159 A | 12/1992 | Dutertre |
| 5,185,066 A | 2/1993 | Golias |
| 5,187,096 A | 2/1993 | Giaever et al. |
| 5,194,300 A | 3/1993 | Cheung |
| 5,194,393 A | 3/1993 | Hugl et al. |
| 5,208,111 A | 5/1993 | Decher et al. |
| 5,221,417 A | 6/1993 | Basavanhally |
| 5,234,809 A | 8/1993 | Boom et al. |
| 5,241,012 A | 8/1993 | Clark |
| 5,244,630 A | 9/1993 | Khalil et al. |
| 5,244,636 A | 9/1993 | Walt et al. |
| 5,244,813 A | 9/1993 | Walt et al. |
| 5,250,264 A | 10/1993 | Walt et al. |
| 5,252,494 A | 10/1993 | Walt |
| 5,254,477 A | 10/1993 | Walt |
| 5,266,238 A | 11/1993 | Haacke et al. |
| 5,266,427 A | 11/1993 | Iwase et al. |
| 5,266,497 A | 11/1993 | Imai et al. |
| 5,281,370 A | 1/1994 | Asher et al. |
| 5,283,079 A | 2/1994 | Wang et al. |
| 5,288,577 A | 2/1994 | Yamaguchi et al. |
| 5,298,741 A | 3/1994 | Walt et al. |
| 5,301,044 A | 4/1994 | Wright |
| 5,306,618 A | 4/1994 | Prober et al. |
| 5,308,586 A | 5/1994 | Fritsche et al. |
| 5,308,749 A | 5/1994 | Sutton et al. |
| 5,320,814 A | 6/1994 | Walt et al. |
| 5,326,691 A | 7/1994 | Hozier |
| 5,326,692 A | 7/1994 | Brinkley et al. |
| 5,329,461 A | 7/1994 | Allen et al. |
| 5,348,853 A | 9/1994 | Wang et al. |
| 5,356,713 A | 10/1994 | Charmot et al. |
| 5,362,653 A | 11/1994 | Carr et al. |
| 5,364,759 A | 11/1994 | Caskey et al. |
| 5,382,512 A | 1/1995 | Smethers et al. |
| 5,382,801 A | 1/1995 | Kanayama |
| 5,389,549 A | 2/1995 | Hamaguchi et al. |
| 5,395,688 A | 3/1995 | Wang et al. |
| 5,405,784 A | 4/1995 | Van Hoegaerden |
| 5,412,087 A | 5/1995 | McGall et al. |
| 5,415,835 A | 5/1995 | Brueck et al. |
| 5,422,246 A | 6/1995 | Koopal et al. |
| 5,436,327 A | 7/1995 | Southern et al. |
| 5,442,246 A | 8/1995 | Azegami et al. |
| 5,444,330 A | 8/1995 | Leventis et al. |
| 5,447,440 A | 9/1995 | Davis et al. |
| 5,468,649 A | 11/1995 | Shah et al. |
| 5,470,534 A | 11/1995 | Imai et al. |
| 5,474,796 A | 12/1995 | Brennan |
| 5,474,895 A | 12/1995 | Ishii et al. |
| 5,480,723 A | 1/1996 | Klainer et al. |
| 5,488,567 A | 1/1996 | Allen et al. |
| 5,496,997 A | 3/1996 | Pope |
| 5,498,392 A | 3/1996 | Wilding et al. |
| 5,510,270 A | 4/1996 | Fodor et al. |
| 5,512,157 A | 4/1996 | Guadagno et al. |
| 5,512,439 A | 4/1996 | Hornes et al. |
| 5,512,490 A | 4/1996 | Walt et al. |
| 5,514,785 A | 5/1996 | VanNess et al. |
| 5,516,635 A | 5/1996 | Ekins et al. |
| 5,518,883 A | 5/1996 | Soini |
| 5,523,231 A | 6/1996 | Reeve |
| 5,527,710 A | 6/1996 | Nacamulli et al. |
| 5,528,392 A | 6/1996 | Nakagawa et al. |
| 5,532,128 A | 7/1996 | Eggers et al. |
| 5,536,648 A | 7/1996 | Kemp et al. |
| 5,545,522 A | 8/1996 | Van Gelder et al. |
| 5,545,531 A | 8/1996 | Rava et al. |
| 5,552,086 A | 9/1996 | Siiman et al. |
| 5,552,270 A | 9/1996 | Khrapko et al. |
| 5,556,752 A | 9/1996 | Lockhart et al. |
| 5,565,324 A | 10/1996 | Still et al. |
| 5,567,304 A | 10/1996 | Datta et al. |
| 5,567,627 A | 10/1996 | Lehnen |
| 5,573,909 A | 11/1996 | Singer et al. |
| 5,582,988 A | 12/1996 | Backus et al. |
| 5,585,069 A | 12/1996 | Zanzucchi et al. |
| 5,587,128 A | 12/1996 | Wilding et al. |
| 5,593,838 A | 1/1997 | Zanzucchi et al. |
| 5,593,839 A | 1/1997 | Hubbell et al. |
| 5,602,042 A | 2/1997 | Farber |
| 5,604,097 A | 2/1997 | Brenner |
| 5,604,099 A | 2/1997 | Erlich et al. |

(56) References Cited

U.S. PATENT DOCUMENTS

| | | |
|---|---|---|
| 5,610,287 A | 3/1997 | Nikiforov et al. |
| 5,627,040 A | 5/1997 | Bierre et al. |
| 5,632,957 A | 5/1997 | Heller et al. |
| 5,633,724 A | 5/1997 | King et al. |
| 5,633,972 A | 5/1997 | Walt et al. |
| 5,637,508 A | 6/1997 | Kidwell et al. |
| 5,639,603 A | 6/1997 | Dower et al. |
| 5,639,606 A | 6/1997 | Willey |
| 5,643,765 A | 7/1997 | Willey |
| 5,648,124 A | 7/1997 | Sutor |
| 5,650,488 A | 7/1997 | O'Hare |
| 5,650,489 A | 7/1997 | Lam et al. |
| 5,652,059 A | 7/1997 | Margel |
| 5,652,107 A | 7/1997 | Lizardi et al. |
| 5,653,939 A | 8/1997 | Hollis et al. |
| 5,660,990 A | 8/1997 | Rao et al. |
| 5,667,667 A | 9/1997 | Southern |
| 5,674,686 A | 10/1997 | Schumm et al. |
| 5,674,698 A | 10/1997 | Zarling et al. |
| 5,679,524 A | 10/1997 | Nikiforov et al. |
| 5,690,894 A | 11/1997 | Pinkel et al. |
| 5,698,271 A | 12/1997 | Liberti et al. |
| 5,700,637 A | 12/1997 | Southern |
| 5,700,897 A | 12/1997 | Klainer et al. |
| 5,714,340 A | 2/1998 | Sutton et al. |
| 5,714,521 A | 2/1998 | Kedem et al. |
| 5,716,852 A | 2/1998 | Yager et al. |
| 5,722,470 A | 3/1998 | Kedar et al. |
| 5,723,218 A | 3/1998 | Haugland et al. |
| 5,723,233 A | 3/1998 | Garza et al. |
| 5,728,529 A | 3/1998 | Metzker et al. |
| 5,736,349 A | 4/1998 | Sasaki et al. |
| 5,744,299 A | 4/1998 | Henrickson et al. |
| 5,744,305 A | 4/1998 | Fodor et al. |
| 5,747,349 A | 5/1998 | Van den Engh et al. |
| 5,751,629 A | 5/1998 | Nova et al. |
| 5,763,175 A | 6/1998 | Brenner |
| 5,763,198 A | 6/1998 | Hirth et al. |
| 5,763,263 A | 6/1998 | Dehlinger |
| 5,766,711 A | 6/1998 | Barmakian |
| 5,766,963 A | 6/1998 | Baldwin et al. |
| 5,770,358 A | 6/1998 | Dower et al. |
| 5,770,367 A | 6/1998 | Southern et al. |
| 5,770,455 A | 6/1998 | Cargill et al. |
| 5,770,721 A | 6/1998 | Ershov et al. |
| 5,773,222 A | 6/1998 | Scott |
| 5,776,711 A | 7/1998 | Vyas et al. |
| 5,779,976 A | 7/1998 | Leland et al. |
| 5,786,219 A | 7/1998 | Zhang et al. |
| 5,789,147 A | 8/1998 | Rubinstein et al. |
| 5,792,430 A | 8/1998 | Hamper |
| 5,800,992 A | 9/1998 | Fodor et al. |
| 5,807,755 A | 9/1998 | Ekins |
| 5,812,272 A | 9/1998 | King et al. |
| 5,814,524 A | 9/1998 | Walt et al. |
| 5,831,045 A | 11/1998 | Stolowitz et al. |
| 5,834,590 A | 11/1998 | Vinik et al. |
| 5,837,501 A | 11/1998 | Beumer et al. |
| 5,837,551 A | 11/1998 | Ekins |
| 5,837,832 A | 11/1998 | Chee et al. |
| 5,840,485 A | 11/1998 | Lebl et al. |
| 5,843,660 A | 12/1998 | Schumm et al. |
| 5,844,304 A | 12/1998 | Kata et al. |
| 5,846,708 A | 12/1998 | Hollis et al. |
| 5,855,753 A | 1/1999 | Trau et al. |
| 5,856,092 A | 1/1999 | Dale et al. |
| 5,858,804 A | 1/1999 | Zanzucchi et al. |
| 5,866,099 A | 2/1999 | Owen et al. |
| 5,866,331 A | 2/1999 | Singer et al. |
| 5,874,219 A | 2/1999 | Rava et al. |
| 5,876,946 A | 3/1999 | Burbaum et al. |
| 5,898,071 A | 4/1999 | Hawkins |
| 5,900,481 A | 5/1999 | Lough et al. |
| 5,922,617 A | 7/1999 | Wang et al. |
| 5,939,021 A | 8/1999 | Hansen et al. |
| 5,942,388 A | 8/1999 | Willner et al. |
| 5,945,525 A | 8/1999 | Uematsu et al. |
| 5,948,621 A | 9/1999 | Turner et al. |
| 5,948,627 A | 9/1999 | Lee et al. |
| 5,952,131 A | 9/1999 | Kumacheva et al. |
| 5,952,174 A | 9/1999 | Nikiforoy et al. |
| 5,959,098 A | 9/1999 | Goldberg et al. |
| 5,961,923 A | 10/1999 | Nova et al. |
| 5,965,235 A | 10/1999 | McGuire et al. |
| 5,965,452 A | 10/1999 | Kovacs |
| 5,968,736 A | 10/1999 | Still et al. |
| 5,981,176 A | 11/1999 | Wallace |
| 5,981,180 A | 11/1999 | Chandler et al. |
| 5,988,432 A | 11/1999 | Sun |
| 5,989,835 A | 11/1999 | Dunlay et al. |
| 5,993,935 A | 11/1999 | Rasmussen et al. |
| 5,994,066 A | 11/1999 | Bergeron et al. |
| 6,001,614 A | 12/1999 | Akhavan-Tafti |
| 6,004,744 A | 12/1999 | Goelet et al. |
| 6,007,996 A | 12/1999 | McNamara et al. |
| 6,013,531 A | 1/2000 | Wang et al. |
| 6,014,451 A | 1/2000 | Berry et al. |
| 6,015,664 A | 1/2000 | Henrickson et al. |
| 6,015,666 A | 1/2000 | Springer et al. |
| 6,017,696 A | 1/2000 | Heller |
| 6,018,350 A | 1/2000 | Lee et al. |
| 6,023,540 A | 2/2000 | Walt et al. |
| 6,023,590 A | 2/2000 | Abe et al. |
| 6,025,905 A | 2/2000 | Sussman |
| 6,027,889 A | 2/2000 | Barany et al. |
| 6,027,945 A | 2/2000 | Smith et al. |
| 6,033,547 A | 3/2000 | Trau et al. |
| 6,043,354 A | 3/2000 | Hillebrand et al. |
| 6,048,690 A | 4/2000 | Heller |
| 6,054,270 A | 4/2000 | Southern |
| 6,060,243 A | 5/2000 | Tang et al. |
| 6,063,569 A | 5/2000 | Gildea et al. |
| 6,068,818 A | 5/2000 | Ackley et al. |
| 6,075,905 A | 6/2000 | Herman et al. |
| 6,077,669 A | 6/2000 | Little et al. |
| 6,077,674 A | 6/2000 | Schleifer et al. |
| 6,080,585 A | 6/2000 | Southern et al. |
| 6,083,699 A | 7/2000 | Leushner et al. |
| 6,083,763 A | 7/2000 | Balch |
| 6,084,991 A | 7/2000 | Sampas |
| 6,086,736 A | 7/2000 | Dasgupta et al. |
| 6,090,458 A | 7/2000 | Murakami |
| 6,090,545 A | 7/2000 | Wohlstadter et al. |
| 6,090,555 A | 7/2000 | Fiekowsky et al. |
| 6,090,912 A | 7/2000 | Lebl et al. |
| 6,096,368 A | 8/2000 | Sun |
| 6,100,030 A | 8/2000 | Feazel et al. |
| 6,103,379 A | 8/2000 | Margel et al. |
| 6,106,685 A | 8/2000 | McBride et al. |
| 6,120,666 A | 9/2000 | Jacobson et al. |
| 6,122,599 A | 9/2000 | Mehta |
| 6,123,263 A | 9/2000 | Feng |
| 6,124,092 A | 9/2000 | O'Neill et al. |
| 6,126,731 A | 10/2000 | Kemeny et al. |
| 6,130,101 A | 10/2000 | Mao et al. |
| 6,132,685 A | 10/2000 | Kercso et al. |
| 6,132,997 A | 10/2000 | Shannon |
| 6,133,436 A | 10/2000 | Koster et al. |
| 6,136,171 A | 10/2000 | Frazier et al. |
| 6,136,468 A | 10/2000 | Mitchell, Jr. et al. |
| 6,139,831 A | 10/2000 | Shivashankar et al. |
| 6,141,046 A | 10/2000 | Roth et al. |
| 6,143,499 A | 11/2000 | Mirzabekov et al. |
| 6,149,789 A | 11/2000 | Benecke et al. |
| 6,150,095 A | 11/2000 | Southern et al. |
| 6,151,062 A | 11/2000 | Inoguchi et al. |
| 6,153,375 A | 11/2000 | Kobylecki et al. |
| 6,153,389 A | 11/2000 | Haarer et al. |
| 6,156,502 A | 12/2000 | Beattie |
| 6,167,910 B1 | 1/2001 | Chow |
| 6,172,218 B1 | 1/2001 | Brenner |
| 6,180,226 B1 | 1/2001 | McArdle et al. |
| 6,183,970 B1 | 2/2001 | Okano et al. |
| 6,187,540 B1 | 2/2001 | Staub et al. |

(56) References Cited

U.S. PATENT DOCUMENTS

| | | |
|---|---|---|
| 6,193,866 B1 | 2/2001 | Bader et al. |
| 6,193,951 B1 | 2/2001 | Ottoboni et al. |
| 6,200,737 B1 | 3/2001 | Walt et al. |
| 6,200,814 B1 | 3/2001 | Malmqvist et al. |
| 6,203,993 B1 | 3/2001 | Shuber et al. |
| 6,207,369 B1 | 3/2001 | Wohlstadter et al. |
| 6,209,589 B1 | 4/2001 | Hare et al. |
| 6,218,111 B1 | 4/2001 | Southern et al. |
| 6,221,598 B1 | 4/2001 | Schumm et al. |
| 6,232,066 B1 | 5/2001 | Felder et al. |
| 6,235,471 B1 | 5/2001 | Knapp et al. |
| 6,238,863 B1 | 5/2001 | Schumm et al. |
| 6,245,508 B1 | 6/2001 | Heller et al. |
| 6,251,592 B1 | 6/2001 | Tang et al. |
| 6,251,595 B1 | 6/2001 | Gordon et al. |
| 6,251,687 B1 | 6/2001 | Buechler et al. |
| 6,251,691 B1 | 6/2001 | Seul |
| 6,254,754 B1 | 7/2001 | Ross et al. |
| 6,254,827 B1 | 7/2001 | Ackley et al. |
| 6,261,430 B1 | 7/2001 | Yager et al. |
| 6,261,782 B1 | 7/2001 | Lizardi et al. |
| 6,264,815 B1 | 7/2001 | Pethig et al. |
| 6,264,825 B1 | 7/2001 | Blackburn et al. |
| 6,266,459 B1 | 7/2001 | Walt et al. |
| 6,267,858 B1 | 7/2001 | Parce et al. |
| 6,268,219 B1 | 7/2001 | Mcbride et al. |
| 6,268,222 B1 | 7/2001 | Chandler et al. |
| 6,271,856 B1 | 8/2001 | Krishnamurthy |
| 6,277,579 B1 | 8/2001 | Lazar et al. |
| 6,280,618 B2 | 8/2001 | Watkins et al. |
| 6,287,778 B1 | 9/2001 | Huang et al. |
| 6,294,063 B1 | 9/2001 | Becker et al. |
| 6,297,062 B1 | 10/2001 | Gombinski |
| 6,303,316 B1 | 10/2001 | Kiel et al. |
| 6,306,643 B1 | 10/2001 | Gentalen et al. |
| 6,307,039 B1 | 10/2001 | Southern et al. |
| 6,309,602 B1 | 10/2001 | Ackley et al. |
| 6,312,134 B1 | 11/2001 | Jain et al. |
| 6,316,186 B1 | 11/2001 | Ekins |
| 6,318,970 B1 | 11/2001 | Backhouse |
| 6,319,472 B1 | 11/2001 | Ackley et al. |
| 6,319,674 B1 | 11/2001 | Fulcrand et al. |
| 6,321,791 B1 | 11/2001 | Chow |
| 6,327,410 B1 | 12/2001 | Walt et al. |
| 6,342,355 B1 | 1/2002 | Hacia et al. |
| 6,349,144 B1 | 2/2002 | Shams |
| 6,355,419 B1 | 3/2002 | Alfenito |
| 6,355,431 B1 | 3/2002 | Chee et al. |
| 6,355,491 B1 | 3/2002 | Zhou et al. |
| 6,358,387 B1 | 3/2002 | Kopf-Sill et al. |
| 6,361,916 B1 | 3/2002 | Chen et al. |
| 6,361,945 B1 | 3/2002 | Becker et al. |
| 6,365,418 B1 | 4/2002 | Wagner et al. |
| 6,368,799 B1 | 4/2002 | Chee |
| 6,387,707 B1 | 5/2002 | Seul et al. |
| 6,399,328 B1 | 6/2002 | Vournakis et al. |
| 6,403,309 B1 | 6/2002 | Iris et al. |
| 6,406,921 B1 | 6/2002 | Wagner et al. |
| 6,426,615 B1 | 7/2002 | Mehta |
| 6,429,027 B1 | 8/2002 | Chee et al. |
| 6,448,012 B1 | 9/2002 | Schwartz |
| 6,451,191 B1 | 9/2002 | Bentsen et al. |
| 6,458,547 B1 | 10/2002 | Bryan et al. |
| 6,468,811 B1 | 10/2002 | Seul |
| 6,480,791 B1 | 11/2002 | Strathmann |
| 6,488,872 B1 | 12/2002 | Beebe et al. |
| 6,494,924 B1 | 12/2002 | Auweter et al. |
| 6,498,863 B1 | 12/2002 | Gaidoukevitch et al. |
| 6,500,620 B2 | 12/2002 | Yu et al. |
| 6,503,680 B1 | 1/2003 | Chen et al. |
| 6,506,564 B1 | 1/2003 | Mirkin et al. |
| 6,509,158 B1 | 1/2003 | Schwartz |
| 6,514,688 B2 | 2/2003 | Muller-Schulte |
| 6,514,714 B1 | 2/2003 | Lee et al. |
| 6,514,771 B1 | 2/2003 | Seul |
| 6,515,649 B1 | 2/2003 | Albert et al. |
| 6,521,747 B2 | 2/2003 | Anastasio et al. |
| 6,528,264 B1 | 3/2003 | Pal et al. |
| 6,531,292 B1 | 3/2003 | Rine et al. |
| 6,531,323 B1 | 3/2003 | Shinoki et al. |
| 6,534,274 B2 | 3/2003 | Becker et al. |
| 6,534,293 B1 | 3/2003 | Barany et al. |
| 6,540,895 B1 | 4/2003 | Spence et al. |
| 6,605,453 B2 | 8/2003 | Ozkan et al. |
| 6,605,474 B1 | 8/2003 | Cole |
| 6,610,256 B2 | 8/2003 | Schwartz |
| 6,620,584 B1 | 9/2003 | Chee et al. |
| 6,642,062 B2 | 11/2003 | Kauvar et al. |
| 6,645,432 B1 | 11/2003 | Anderson et al. |
| 6,650,703 B1 | 11/2003 | Schwarzmann et al. |
| 6,670,128 B2 | 12/2003 | Smith et al. |
| 6,692,914 B1 | 2/2004 | Klaerner et al. |
| 6,703,288 B2 | 3/2004 | Nagasawa et al. |
| 6,706,163 B2 | 3/2004 | Seul et al. |
| 6,713,309 B1 | 3/2004 | Anderson et al. |
| 6,730,515 B2 | 5/2004 | Kocher |
| 6,743,581 B1 | 6/2004 | Vo-Dinh |
| 6,760,157 B1 | 7/2004 | Allen et al. |
| 6,779,559 B2 | 8/2004 | Parce et al. |
| 6,797,524 B1 | 9/2004 | Seul |
| 6,806,050 B2 | 10/2004 | Zhou et al. |
| 6,812,005 B2 | 11/2004 | Fan et al. |
| 6,824,981 B2 * | 11/2004 | Chait et al. .................. 435/6.11 |
| 6,838,289 B2 | 1/2005 | Bell et al. |
| 6,844,156 B2 | 1/2005 | Rosen |
| 6,869,798 B2 | 3/2005 | Crews et al. |
| 6,887,701 B2 | 5/2005 | Anderson et al. |
| 6,890,741 B2 | 5/2005 | Fan et al. |
| 6,897,271 B1 | 5/2005 | Domschke et al. |
| 6,905,881 B2 | 6/2005 | Sammak et al. |
| 6,908,737 B2 | 6/2005 | Ravkin et al. |
| 6,942,968 B1 | 9/2005 | Dickinson et al. |
| 6,955,751 B1 | 10/2005 | Seul |
| 6,955,889 B1 | 10/2005 | Mercolino et al. |
| 6,955,902 B2 | 10/2005 | Chumakov et al. |
| 6,958,245 B2 | 10/2005 | Seul et al. |
| 6,991,941 B1 | 1/2006 | Seul |
| 6,993,156 B1 | 1/2006 | Szeliski et al. |
| 7,015,047 B2 | 3/2006 | Huang et al. |
| 7,041,453 B2 | 5/2006 | Yang |
| 7,049,077 B2 | 5/2006 | Yang |
| 7,056,746 B2 | 6/2006 | Seul et al. |
| 7,060,431 B2 | 6/2006 | Chee et al. |
| 7,090,759 B1 | 8/2006 | Seul |
| 7,097,974 B1 | 8/2006 | Stahler et al. |
| 7,099,777 B1 | 8/2006 | Ghandour |
| 7,115,884 B1 | 10/2006 | Walt et al. |
| 7,132,239 B2 | 11/2006 | Livak et al. |
| 7,141,217 B2 | 11/2006 | Karlsson et al. |
| 7,144,119 B2 | 12/2006 | Seul et al. |
| 7,157,228 B2 | 1/2007 | Hashmi et al. |
| 7,195,913 B2 | 3/2007 | Guire et al. |
| 7,229,840 B1 | 6/2007 | Wischerhoff |
| 7,262,016 B2 | 8/2007 | Huang et al. |
| 7,291,504 B2 | 11/2007 | Seul |
| 7,306,918 B2 | 12/2007 | Hashmi et al. |
| 7,320,864 B2 | 1/2008 | Yang |
| 7,335,153 B2 | 2/2008 | Seul et al. |
| 7,344,841 B2 | 3/2008 | Hashmi et al. |
| 7,358,097 B2 | 4/2008 | Seul et al. |
| 7,390,676 B2 | 6/2008 | Seul et al. |
| 7,425,416 B2 | 9/2008 | Hashmi et al. |
| 7,427,512 B2 | 9/2008 | Seul |
| 7,501,253 B2 | 3/2009 | Pourmand et al. |
| 7,526,114 B2 | 4/2009 | Xia et al. |
| 7,582,488 B2 | 9/2009 | Banerjee et al. |
| 7,595,279 B2 | 9/2009 | Wang et al. |
| 7,615,345 B2 | 11/2009 | Seul |
| 7,732,575 B2 | 6/2010 | Wang et al. |
| 7,737,088 B1 | 6/2010 | Stahler et al. |
| 7,749,774 B2 | 7/2010 | Seul |
| 7,790,380 B2 | 9/2010 | Yang |
| 7,848,889 B2 | 12/2010 | Xia et al. |
| 7,940,968 B2 | 5/2011 | Seul et al. |

(56) References Cited

U.S. PATENT DOCUMENTS

| | | |
|---|---|---|
| 2001/0034614 A1 | 10/2001 | Fletcher-Haynes et al. |
| 2001/0044531 A1 | 11/2001 | McGall et al. |
| 2001/0046602 A1 | 11/2001 | Chandler et al. |
| 2001/0049095 A1 | 12/2001 | Webster |
| 2002/0006634 A1 | 1/2002 | Han et al. |
| 2002/0015952 A1 | 2/2002 | Anderson et al. |
| 2002/0022276 A1 | 2/2002 | Zhou et al. |
| 2002/0029235 A1 | 3/2002 | Lock et al. |
| 2002/0031841 A1 | 3/2002 | Asher et al. |
| 2002/0032252 A1 | 3/2002 | Ishizuka |
| 2002/0039728 A1 | 4/2002 | Kain et al. |
| 2002/0045169 A1 | 4/2002 | Shoemaker et al. |
| 2002/0081714 A1 | 6/2002 | Jain et al. |
| 2002/0102567 A1 | 8/2002 | Fodor et al. |
| 2002/0125138 A1 | 9/2002 | Medoro |
| 2002/0127603 A1 | 9/2002 | Basiji et al. |
| 2002/0137074 A1 | 9/2002 | Piunno et al. |
| 2002/0142318 A1 | 10/2002 | Cattell et al. |
| 2002/0150909 A1 | 10/2002 | Stuelpnagel et al. |
| 2002/0155481 A1 | 10/2002 | Hirota et al. |
| 2002/0166766 A1 | 11/2002 | Seul et al. |
| 2002/0182609 A1 | 12/2002 | Arcot |
| 2002/0187501 A1 | 12/2002 | Huang et al. |
| 2002/0197728 A1 | 12/2002 | Kaufman et al. |
| 2002/0198665 A1 | 12/2002 | Seul et al. |
| 2003/0003272 A1 | 1/2003 | Laguitton |
| 2003/0004594 A1 | 1/2003 | Liu et al. |
| 2003/0006143 A1 | 1/2003 | Banerjee et al. |
| 2003/0012693 A1 | 1/2003 | Otillar et al. |
| 2003/0012699 A1 | 1/2003 | Moore et al. |
| 2003/0022370 A1 | 1/2003 | Casagrande et al. |
| 2003/0022393 A1 | 1/2003 | Seul et al. |
| 2003/0031351 A1 | 2/2003 | Yim |
| 2003/0038812 A1 | 2/2003 | Bartell |
| 2003/0040129 A1 | 2/2003 | Shah |
| 2003/0062422 A1 | 4/2003 | Fateley et al. |
| 2003/0077607 A1 | 4/2003 | Hopfinger et al. |
| 2003/0082487 A1 | 5/2003 | Burgess |
| 2003/0082530 A1 | 5/2003 | Soderlund et al. |
| 2003/0082531 A1 | 5/2003 | Soderlund et al. |
| 2003/0082587 A1 | 5/2003 | Seul et al. |
| 2003/0087228 A1 | 5/2003 | Bamdad et al. |
| 2003/0108913 A1 | 6/2003 | Schouten |
| 2003/0129296 A1 | 7/2003 | Kelso |
| 2003/0134326 A1 | 7/2003 | Hansen et al. |
| 2003/0138842 A1 | 7/2003 | Seul et al. |
| 2003/0148335 A1 | 8/2003 | Shen et al. |
| 2003/0152931 A1 | 8/2003 | Chiou et al. |
| 2003/0154108 A1 | 8/2003 | Fletcher-Haynes et al. |
| 2003/0177036 A1 | 9/2003 | Oka et al. |
| 2003/0182068 A1 | 9/2003 | Battersby et al. |
| 2003/0186220 A1 | 10/2003 | Zhou et al. |
| 2003/0228610 A1 | 12/2003 | Seul |
| 2004/0002073 A1 | 1/2004 | Li et al. |
| 2004/0009614 A1 | 1/2004 | Ahn et al. |
| 2004/0014073 A1 | 1/2004 | Trau et al. |
| 2004/0048259 A1 | 3/2004 | Hashmi et al. |
| 2004/0087032 A1* | 5/2004 | Chandler et al. ............. 436/164 |
| 2004/0093238 A1 | 5/2004 | Deakter |
| 2004/0106121 A1 | 6/2004 | Ugolin et al. |
| 2004/0132122 A1 | 7/2004 | Banerjee et al. |
| 2004/0137641 A1 | 7/2004 | Holtlund et al. |
| 2004/0175734 A1 | 9/2004 | Stahler et al. |
| 2004/0219520 A1 | 11/2004 | Mirkin et al. |
| 2004/0229269 A1 | 11/2004 | Hashmi et al. |
| 2005/0048570 A1 | 3/2005 | Weber et al. |
| 2005/0112585 A1 | 5/2005 | Zichi et al. |
| 2005/0143928 A1 | 6/2005 | Moser et al. |
| 2005/0239098 A1 | 10/2005 | Hastings et al. |
| 2006/0024732 A1 | 2/2006 | Huang et al. |
| 2006/0035240 A1 | 2/2006 | Seul et al. |
| 2006/0275799 A1 | 12/2006 | Banerjee et al. |
| 2007/0031877 A1 | 2/2007 | Stahler et al. |
| 2007/0231810 A1 | 10/2007 | Todd et al. |
| 2007/0243534 A1 | 10/2007 | Seul et al. |
| 2008/0020374 A1 | 1/2008 | Greene et al. |
| 2008/0123089 A1 | 5/2008 | Seul et al. |
| 2008/0200349 A1 | 8/2008 | Wu et al. |
| 2008/0214412 A1 | 9/2008 | Stahler et al. |
| 2008/0261205 A1 | 10/2008 | Denomme |
| 2010/0062518 A1 | 3/2010 | Banerjee |

FOREIGN PATENT DOCUMENTS

| | | |
|---|---|---|
| EP | 0126450 | 11/1984 |
| EP | 179039 | 4/1986 |
| EP | 246864 | 11/1987 |
| EP | 269764 | 6/1988 |
| EP | 472990 | 3/1992 |
| EP | 478319 | 4/1992 |
| EP | 0529775 | 3/1993 |
| EP | 1394270 | 3/2004 |
| EP | 1564306 | 2/2005 |
| JP | 62265567 | 11/1987 |
| JP | 03-236777 | 10/1991 |
| WO | WO8911101 | 5/1989 |
| WO | WO 9109141 | 6/1991 |
| WO | WO 9119023 | 12/1991 |
| WO | WO 9210092 | 6/1992 |
| WO | WO 9325563 | 6/1992 |
| WO | WO 9302360 | 2/1993 |
| WO | WO 9306121 | 4/1993 |
| WO | WO 9324517 | 12/1993 |
| WO | WO 9400810 | 1/1994 |
| WO | WO 9428028 | 9/1994 |
| WO | WO 9509248 | 4/1995 |
| WO | WO 9512608 | 5/1995 |
| WO | WO 9512808 | 5/1995 |
| WO | WO 9600148 | 1/1996 |
| WO | WO 9602558 | 2/1996 |
| WO | WO 9603212 | 2/1996 |
| WO | WO 9604547 | 2/1996 |
| WO | WO 9607917 | 3/1996 |
| WO | WO 9630392 | 10/1996 |
| WO | WO9641011 | 12/1996 |
| WO | WO 9714028 | 4/1997 |
| WO | WO 9722720 | 6/1997 |
| WO | WO 9739151 | 10/1997 |
| WO | WO 9740383 | 10/1997 |
| WO | WO 9740385 | 10/1997 |
| WO | WO 9745559 | 12/1997 |
| WO | WO 9802752 | 1/1998 |
| WO | WO 9804950 | 2/1998 |
| WO | WO 9806007 | 2/1998 |
| WO | WO 9820153 | 5/1998 |
| WO | WO 9821593 | 5/1998 |
| WO | WO 9838334 | 9/1998 |
| WO | WO 9840726 | 9/1998 |
| WO | WO 9853093 | 11/1998 |
| WO | WO 9909217 | 2/1999 |
| WO | WO 9918434 | 4/1999 |
| WO | WO 9919515 | 4/1999 |
| WO | WO 9924822 | 5/1999 |
| WO | WO 9935499 | 7/1999 |
| WO | WO 9936564 | 7/1999 |
| WO | WO 9941273 | 8/1999 |
| WO | WO 9951773 | 10/1999 |
| WO | WO 9960170 | 11/1999 |
| WO | WO 9967641 | 12/1999 |
| WO | WO 0003004 | 1/2000 |
| WO | WO 0004372 | 1/2000 |
| WO | WO 0007019 | 2/2000 |
| WO | WO 0013004 | 3/2000 |
| WO | WO 0020593 | 4/2000 |
| WO | WO 0022172 | 4/2000 |
| WO | WO 0026920 | 5/2000 |
| WO | WO 0031356 | 6/2000 |
| WO | WO 0039587 | 7/2000 |
| WO | WO 0046602 | 8/2000 |
| WO | WO 0051058 | 8/2000 |
| WO | WO 0062048 | 10/2000 |
| WO | WO 0073777 | 12/2000 |
| WO | WO 0075373 | 12/2000 |
| WO | WO 0101184 | 1/2001 |

(56) References Cited

FOREIGN PATENT DOCUMENTS

| | | |
|---|---|---|
| WO | WO 0120179 | 3/2001 |
| WO | WO 0136679 | 5/2001 |
| WO | WO 0154813 | 8/2001 |
| WO | WO 0156216 | 8/2001 |
| WO | WO 0184150 | 11/2001 |
| WO | WO 0188535 | 11/2001 |
| WO | WO 0194947 | 12/2001 |
| WO | WO 0198765 | 12/2001 |
| WO | WO 0212888 | 2/2002 |
| WO | WO 0214864 | 2/2002 |
| WO | WO 0231182 | 4/2002 |
| WO | WO 0233084 | 4/2002 |
| WO | WO 0235441 | 5/2002 |
| WO | WO 0237209 | 5/2002 |
| WO | WO02057496 | 7/2002 |
| WO | WO02058379 | 7/2002 |
| WO | WO02061121 | 8/2002 |
| WO | WO 02079490 | 10/2002 |
| WO | WO 02084285 | 10/2002 |
| WO | WO 02096979 | 12/2002 |
| WO | WO 03020968 | 3/2003 |
| WO | WO 03025011 | 3/2003 |
| WO | WO 03034029 | 4/2003 |
| WO | WO 03058196 | 7/2003 |
| WO | WO 03079401 | 9/2003 |
| WO | WO 03092546 | 11/2003 |
| WO | WO 2004035426 | 4/2004 |
| WO | WO 2005000236 | 1/2005 |
| WO | WO 2005042763 | 5/2005 |
| WO | WO 2005045059 | 5/2005 |
| WO | WO 2005095650 | 10/2005 |
| WO | WO 2008040257 | 4/2008 |
| WO | WO 2009088893 | 7/2009 |
| WO | WO 2010025002 | 3/2010 |
| WO | WO2010026038 | 3/2010 |
| WO | WO2010098765 | 9/2010 |
| WO | WO 2010143678 | 12/2010 |

OTHER PUBLICATIONS

Armstrong et al., "Suspension arrays for high throughput, multiplexed single nucleotide polymorphism genotyping" Cytometry. vol. 40:102-108 (2000).

Bortolin, S. et al. "Analytical validation of the tag-it high-throughput microsphere-based universal arrray genotyping platform: application to the multiplex detection of a panel of thrombophilia-associated single-nucleotide polymorphisms" Clinical Chemistry, vol. 50 (11), pp. 2028-2036 (Sep. 13, 2004).

B.-Y. Ha et al., "Counterion-Mediated Attraction between Two Like-Charged Rods," Physical Review Letters, Aug. 18, 1997, vol. 79, No. 7, pp. 1289-1292.

A. Hatch, et al., "Diffusion Immunoassay in Polyacrylamide Hydrogels". Micro Total Analysis Systems, pp. 571-572 (2001).

Aho et al., "Efficient String Matching: An Aid to Bibliographic Search". Communications of the ACM, vol. 18, No. 6, pp. 333-340 (Jun. 1975).

Albergo et al., "Solvent effects on the thermodynamics of double-helix formation in (dG-sC) 3". Biochemistry, vol. 20, No. 6: 1413-1418 (1981).

Albrecht et al, "Probing the role of multicellular organization in three-dimensional microenvironments". Nature Methods, vol. 3, No. 5, pp. 369-375 (May 2006).

Albrecht et al., "Photo and electropatterning of hydrogel-encapsulated living cell arrays", Lab on a Chip, vol. 5, Issue 1, pp. 111-118 (2004).

Alford, R. L., "DNA Analysis in forensics, disease and animal/plant identification". Current Opinions in Biotechnology, vol. 5(1), pp. 29-33 (1994).

Al-Soud, W. A., "Purification and Characterization of PCR-Inhibitory Components in Blood Cells". Journal of Clinical Microbiology, vol. 39, No. 2, pp. 485-493 (Feb. 2001).

Al-Soud, W. A., et al., "Identification and characterization of immunoglobulin G in blood as a major inhibitor of diagnostic PCR". Journal of Clinical Microbiology, vol. 38, No. 1, pp. 345-350 (Jan 2000).

Ambruso, D. R., et al., "Experience with donors matched for minor blood group antigens in patients with sickle cell anemia who are receiving chronic transfusion therapy", Transfusion, vol. 27, No. 1, 1987, pp. 94-98.

Zhang, Y., et al., "Reproducible and inexpensive probe preparation for oligonucleotide arrays". Nucleic Acids Research, vol. 29, No. 13, pp. E66-6 (Jul. 1, 2001).

Arenko, et al., "Protein microchips: Use for immunoassay and enzymatic reactions". Analytical Biochemistry, vol. 278, pp. 123-131 (2000).

Assie et al., Correlation between low/high affinity ratios for 5-HT Receptors and Intrinsic Activity, European Journal of Pharmacology, vol. 386, pp. 97-103 (1999).

Bakewell et al., "Characterization of the dielectrophoretic movement of DNA in micro-fabricated structures", Institute of Physics Conference Series (1999) Electrostatics (1999).

Balass et al. "Recovery of high-affinity phage from a Nitrostretavidin matrix in phage-display technology". Analytical Biochemistry. vol. 243: 264-269 (1996).

Baldwin, et al., "Phosphorylation of gastrin-17 by epidermal growth factor-stimulated tyrosine kinase". Nature, vol. 44, pp. 2403-2404 (1998).

Bandeira-Melo, C., et al., "EliCell: A gel-phase dual antibody capture and detection assay to measure cytokine release from eosinophils". Journal of Immunological Methods, vol. 244, pp. 105-115 (2000).

Bao, Y. P., et al., "Detection of Protein Analytes via Nanoparticle-Based Bio Bar Code Technology". Anal. Chem., vol. 78, pp. 2055-2059 (2006).

Barany, Francis, "Genetic Disease Detection and DNA Amplification using Cloned Thermostable Ligase". Proceedings of the National Academy of Sciences of the United States of America, vol. 88, pp. 189-193 (Jan. 1991).

Barnard et al. "A fibre-optic chemical sensor with descrete sensing sites". Nature, vol. 353:338-340 (1991).

Basu, S., et al., "Synthesis and Characterization of a Peptide Nucleic Acid Conjugated to a D-Peptide Analog of Insulin-like Growth Factor 1 for Increased Cellular Uptake". Bioconjugate Chem, vol. 8, No. 4, pp. 481-488 (1997).

Battersby et al., "Toward Larger Chemical Libraries: Encoding with Fluorescent Colloids in Combinatorial Chemistry". J. Amer Chem Soc, vol. 122, pp. 2138-2139 (2000).

Baumgarth N. et al., A practical approach to multicolor flow cytometry for immunophenotyping, J. Immunological Methods, 2000, pp. 77-97, vol. 243.

Bavykin, S.G., et al., "Portable system for microbial sample preparation and oligonucleotide microarray analysis". Appl. Environmental Microbiol. 67(2), 922-928 (2001).

Beatty et al. "Probability of Finding HLA-mismatched Related or Unrelated Marrow or Cord Blood Donors", Human Immunology, 2001, vol. 61, pp. 834-840.

Beebe et al., "Functional Hydrogel structures for autonomous flow control inside microfluidic channels". Nature, vol. 404, No. 6778, pp. 588-590 (Apr. 6, 2000).

Beiboer, S. W., et al., "Rapid genotyping of blood group antigens by multiplex polymerase chain reaction and DNA microarray hybridization" 45 Transfusion 667-679 (2005).

Bennett, P. R., et al., "Prenatal Determination of Fetal RhD Type by DNA Amplification". The New England Journal of Medicine, vol. 329, No. 9, pp. 607-610 (Aug. 26, 1993).

Bernard, Philip S., "Homogenous Multiplex Genotyping of Hemochromatasis Mutations with Fluorescent Hybridization Probes". American Journal of Pthology, vol. 153, No. 4, pp. 1055-1061 (1998).

Bessetti, J., "An introduction to PCT Inhibitors". Profiles in DNA-PCR Inhibition, pp. 9-10 (Mar. 2007).

Bickel, P. J., "Discussion of the Evaluation of Forensic DNA Evidence". Proc. Natl. Acad. Sci., vol. 94, p. 5497 (May 1997).

(56) References Cited

OTHER PUBLICATIONS

Zhang, X., et al., "Strand invasion by mixed base PNAs and a PNA-peptide chimera". Nucleic Acids Research, vol. 28, No. 17, pp. 3332-3338 (2000).
Blaaderen, et al., "Synthesis and Characterization of Colloidal Dispersions of Fluorescent, Monodisperse Silica Spheres". Langmuir, vol. 8, No. 2, pp. 2921-2931 (1992).
Bonnet, G., et al., "Thermodynamic basis of the enhanced specificity of structured DNA probes," Proc. Natl. Acad. Science, USA, vol. 96, pp. 6171-6176, May 1999.
Bos et al., "Controlled release of pharmaceutical protein from hydrogels". Business Briefing: Pharmatech, pp. 184-187 (2002).
Boyce, et al. "Peptidosteroidal Receptors for Opioid Peptides. Sequence-Selective Binding Using a Synthetic Receptor Library". J. Am. Chem. Soc., vol. 116, No. 17, pp. 7955-7956 (1994).
Boyd et al. "Tosyl Chloride activation of a rayon/polyester cloth for protein immobilization", Biotechnology Techniques, Apr. 1993, vol. 7, 4:277-282.
Braga et at, "Hydrophobic Polymer Modification with Ionic Reagents: Polysterene Staining with Water-Soluble Dyes". Langmuir, vol. 19, No. 18, pp. 7580-7586 (2003).
Breslauer, K.J. et al., "Predicting DNA duplex stability from the base sequence". PNAS USA, vol. 83, pp. 3746-3750 (1986).
Brick, et al., "Formation of Colloidal Dispersions of Organic Materials in Aqueous Media by Solvent Shifting". Langmuir, vol. 19, No. 16, pp. 6367-6380 (Jan. 31, 2003).
Broude et al., "Multiplex allele-specific target amplification based on PCR suppression". PNAS. vol. 98, No. 1, pp. 206-211 (2001).
Brown, Patrick O., et al., "Exploring the new world of the genome with DNA microarrays". Nature Genetics Supplement, vol. 21, pp. 33-37 (Jan. 1999).
Buck et al., "Design Strategies and Performance of Custom DNA Sequence Primers". BioTechniques, vol. 27, pp. 528-536 (Sep. 1999).
Bunce et al., "Phototyping: Comprehensive DNA Typing for HLA-A, B, C, DRB1, DRB2, DRB3, DRB4, DRB5 & DQB1 by PCR with 144 primer mixes utilizing sequence-specific primers (PCR-SSP)". Tissue Antigens, vol. 46, No. 5, pp. 355-367 (Nov. 1995).
Bunce, M., et al., "Comprehensive serologically equivalent DNA typing for HLA-A by PCR using sequence specific primers (PCR_SSP)", Tissue Anitigens 45 : 81-90 (1995).
Burbulis, I, et al., "Using protein-DNA chimeras to detect and count small numbers of molecules". Nature Methods, vol. 2, No. 1, pp. 31-37 (Jan. 2005).
Cai et al., "Flow cytometry-based minisequencing: A new platform for high-throughput single-nucleotide polymorphism scoring", Genomics 66:135-143 (2000).
Campbell, C. J., et al., "Cell Interaction Microarray for Blood Phenotyping". Analytical Chemistry, vol. 78, pp. 1930-1938 (2006).
Campian et al. Colored and fluorescent solid supports. Innovation and Perspectives in Solid Phase Synthesis. Ed: E. Birmingham (Mayflower, London), pp. 469-474 (1994).
Cao et al., "High and intermediate resolution DNA typing systems for class I HLA-A, B, C genes by hybridization with sequence-specific oligonucleotide probes (SSOP)", Rev Immunogenetics 1:177-208 (1999).
Cao et al., "Nanoparticles with Raman Spectroscopic Fingerprints for DNA and RNA Detection" , Science 197:1536-1539 (2002).
Caruso et al., "Magnetic Core-Shell Particles: Preparation of Magnetite Multilayers on Polymer Latex Microspheres". Advanced materials, vol. 11, No. 11, pp. 950-953 (1999).
Caruso, et al., "Magnetic Nanocomposite Particles and Hollow Spheres Constructed by a Sequential Layering Approach". Chem Mater, vol. 13, No. 1, pp. 109-116 (2001).
Caruso. "Nanoengineering of Particle Surfaces". Advanced Materials, vol. 12, No. 1, pp. 11-22 (2001).
Casnellie JE, et al., "Phosphorylation of synthetic peptides by a tyrosine protein kinase from the particulate fraction of a lymphoma cell line". Proc natl Sci USA, vol. 79, No. 2, pp. 282-286 (1982).

Chalmers, et al., "An instrument to determine the magnetophoretic mobility of labeled, biological cells and paramagnetic particles". Journal of Magnetism and Magnetic Materials, vol. 194, pp. 231-241 (1999).
Chan et al. The Bipohysics of DNA Hybridization with Immobilized Oligonucleotide Probes. Biophysical Journal 69: pp. 2243-2255 (1995).
Chang, et al., "New Approach to Produce monosized Polymer Microcapsules by the Solute Co-diffusion Method". Langmuir, vol. 17, No. 18, pp. 5435-5439 (2001).
Zhang et al., "Reconstruction of DNA sequencing by hybridization". Bioinformatics, vol. 19, No. 1, pp. 14-21 (2003).
Chaudhry et al., "Reactivity of human apurinic/apyrimidinic endonucleoase and *Escheria coli* exonucleonase III with bistranded abasic sites in DNA". The Journal of Biological Chemisty., vol. 272: 15650-15655 (1997).
Chee, M. et al., "Accessing genetic information with high-density DNA arrays". Science, vol. 274, pp. 610-613 (1996).
Chen et al., "A Microsphere-Based assay for multiplexed single nucleotide polymorphism analysis using single base chain extension", Genome Research, Cold Spring Harbor Laboratory Press 10:549-557 (2000).
Zhang et al., "Nuclear DNA analysis in genetic studies of populations; practice, problems and prospects" Molecular Ecology. vol. 12:563-584 (2003).
Chen, YX, et al., "Deletion of arginine codon 229 in the Rhce gene alters e and f but not c antigen expression". vol. 44, No. 3, pp. 391-398 (Mar. 2004).
Cheng, et al., "A Synthetic peptide derived from p34cdc2 is a Specific and Efficient Substrate of SRC-Family Tyrosine Kinases". J Biol Chem, pp. 9248-9256. vol. 267, No. 13 (1992).
Zborowski, et al., "Continuous cell separation using novel magnetic quadruple flow sorter". Journal of Magnetism and Magnetic Materials, vol. 194, pp. 224-230 (1999).
Cherepinsky, Vera, "On mathematical aspects of genomic analysis", Ph.D. Thesis, published Mar. 2004.
Cheung, V. G., et al., "Making and Reading Microarrays". vol. 21, pp. 15-19 (Jan. 1999).
Choi, et al., "An on-chip magnetic separator using spiral electromagnets with semi-encapsulated permalloy". Biosensors & Bioelectronics, vol. 16, pp. 409-416 (2001).
Yellen, B. B., et al., "Programmable Assembly of Colloidal Particles Using Magnetic Microwell Templates". Langmuir, p. est 6.5 (2004).
Clerc, P., et al., "Advanced deep reactive ion etching: a versatile tool for microelectromechanical systems". J. Micromech Microeng, vol. 8, No. 4, pp. 272-278 (Dec. 1998).
Coffer et al., "Characterization of Quanum-Confined CdS Nanocrystallites Stabilized by Deoxyribonucleic Acid (DNA)" Nanotechnology, 1992 3:69-75.
Yeh, S. R., et al., "Assembly of ordered colloidal aggregares by electric-field-induced fluid flow". Nature, Mar. 6, 1997; vol. 386, No. 6620, pp. 57-59.
Colombie, et al., "Role of Mixed Anionic-Nonionic Systems of Surfactants in the Emulsion Polymerization of Styrene: Effect on Particle Nucleation". Macromolocules, vol. 33, No. 20, pp. 7283-7291 (2000).
Cosgrove et al. "A Small-angle neutron scattering study of the structure of gelatin at the surface of polystyrene latex particles". Langmuir. vol. 14:5376-5382 (1998).
Coyne et al., "Assymetric PCR for ssDNA Production", Molecular Biology Techniques Manual. Third Edition. Jan. 1994, Feb. 2001; http://www.mcb.uct.ac.za/pcrcond.htm.
Crisp, M., et al., "Preparation of Nanoparticle Coatings on Surfaces of Complex Geometry". Nano Letters, vol. 3, No. 2, pp. 173-177 (2003).
Cronin M.T. et al., "Cystic Fibrosis Mutation Detection by Hybridization to Light-Generated DNA Probe Arrays," Human Mutation, John Wiley & Sons, Inc., US, vol. 7, No. 3, pp. 244-255 (Jan. 1996).
Cruse et al., "Illustrated Dictionary of Immunology". Boca Raton: CRC Press, p. 512 (2003).

(56) References Cited

OTHER PUBLICATIONS

Dai-Wu Seol, et al., "Signaling Events Triggered by Tumor Necrosis Factor-related Apoptosis-inducing Ligand (TRAIL): Caspase-8 is Required for TRAIL-Induced Apoptosis". Cancer Research, vol. 61, pp. 1138-1143 (2001).
Dasgupta, et al., "Flow of multiple fluids in a smalll dimension". Analytical Chemistry, vol. 74, No. 7, pp. 208-213 (2002).
De Farias, P., et al., Investigation of red blood cell antigens with highly fluorescent and stable semiconductor quantum dots, J. Bimedical Optics, 2005, pp. 1-4, vol. 10(4).
Decher, G., "Fuzzy Nanoassemblies: Toward Layered Polymeric Multicomposites". Science, vol. 277, pp. 1232-1237 (Aug. 29, 1997).
Denomme, G. A., et al., "High throughput multiplex single-nucloetide polymorphism analysis for red cell and platelet antigen genotypes". Transfusion, vol. 45, pp. 660-666 (May 2005).
Denkov et al. "Mechanism of Formation of Two-Dimensional Crystals from Latex Particles on Substrates," langmuir, 1992, pp. 3183-3190, vol. 8.
Ding et al., "Direct molecular haplotyping of long-range genomic DNA with M1-PCR", Jun. 2003, vol. 100, 13: 7449-7453.
Du et al., "Sensitivity and Specificity of Metal Surface-Immobilized," Molecular Beacon, Biosensors; JACS 2005, vol. 127, No. 21, pp. 7932-7940.
Duggan, David J., et al., "Expression profiling using cDNA microarrays". Nature Genetics Supplement, vol. 21, pp. 10-14 (Jan. 1999).
Dunbar SA et al. "Application of the luminex LabMAP in rapid screening for mutations in the cystic fibrosis transmembrane conductance regulator gene: A pilot study" Clin Chem Sep. 2000; 46(9): 1498-500. with Abstract data, pp. 1 and 2.
Duquesnoy HLA Matchmaker: A Molecularly Based Algorithm for Histocompatibility Determination. I. Description of the Algorithm. Human Immunology, vol. 63, pp. 339-352 (2002).
Dziennik, S. R., et al., "Nondiffusive mechanisms enhance protein uptake rates in ion exchange particles". PNAS, vol. 100, No. 2, pp. 420-425 (2003).
Easteal, S. "DNA Fingerprinting by PCR Amplification of HLA Genes". DNA and Criminal Justice; Human Genetics Group, John Curtin School of Medical Research, pp. 121-127 (1991).
Egner et al. "Tagging in combinatorial chemistry: the use of coloured and fluorescent beads". Chem. Commun. pp. 735-736 (1997).
Elaissari et al., "Hydrophilic and cationic latex particles for the specific extraction of nucleic acids". J. Biomater, Sci Polymer Edn, vol. 10, pp. 403-420 (1999).
Erdogan et al., "Detection of mitochondrial single nucleotide polymorphisms using a primer elongation reaction on oligonucleotide microarrays", Nucleic Acid Research, 29 : 1-7 (2001).
Ericsson, O., et al., "A dual-tag microarray platform for high-performance nucleic acid and protein analyses". Nucleic Acids Research, vol. 36, No. 8 e45, pp. 1-9 (2008).
Erlich, et al., "HLA DNA Typing and Transplantation", Immunity, 14: 347-356 (2001).
Fan et al., "Parallel Genotyping of Human SNPs Using Generic High-density Oligonucleotide Tag Arrays", Genome Research, vol. 10, pp. 853-860 (2000).
Fatin-Rouge, N., et al., "Diffusion and Partitioning of Solutes in Agarose Hydrogels: The Relative Influence of Electrostatic and Specific Interactions", J. Phys. Chem. B., vol. 107, pp. 12126-12137 (2003).
Ferguson et al., "High-Density Fiber-Optic DNA Random Microsphere Array". Anal. Chem, vol. 72, pp. 5618-5624 (2000).
Filipovich et al., "Impact of donor type on outcome of bone marrow transplantation for Wiskott-Aldrich syndrome: collaborative study of the International Bone Marrow Transplant Registry and the National Marrow Donor Program", Blood, vol. 97, No. 6, pp. 1598-1603 (2001).
Finkel, et al. "Barcoding the Microworld". Analytical Chemistry, pp. 353-359 (Oct. 1, 2004).
Fitch, J.P. et al., "Rapid Development of Nucleic Acid Diagnostics", Proceedings of the IEEE 90 (11): 1708-1720 (Nov. 2002).
Fluorescent Microspheres (Tech. Note #19). Bangs Laboratories (1997).
Fodor, S,, et al., "Light-Directed, Spatially Addressable Parallel Chemical Synthesis". Research Article (Authors are at the Affymax Research Institute, 3180 Porter Drive, Palo Alto, CA 94304), pp. 767-773 (Feb. 15, 1991).
Fowke, Keith R., et al. "Genetic analysis of human DNA recovered from minute amounts of serum or plasma". Journal of Immunological Methods, vol. 80, pp. 45-51 (1995).
Frengen, Jomar, et al., "Demonstration and Minimization of Serum Interference in Flow Cytometric Two-Site Immunoassays". Clinical Chemistry, vol. 40, No. 3, pp. 420-425 (1994).
Fuh et al. Single Fibre Optic Fluorescence pH Probe. Analyst, 112:1159-1163 (1987).
Fuh et al., "A Method for Determination of Particle Magnetic Susceptibility with Analytical Magnetapheresis". Anal. Chem, vol. 72, pp. 3590-3595 (2000).
Fulton et al. "Advanced multiplexed analysis with the FlowMetrix system". Clinical Chemistry, vol. 43:9, pp. 1749-1756 (1997).
Gahan, P. B., "Circulating Nucleic Acid in Plasma and Serum: Diagnosis and Prognosis in Cancer". Oncology, vol. 32, No. 6, pp. 20-22 (Oct. 2008); Weekly news updates on www.cli-online.com.
Garber, K. "More SNPs on the Way". Science, vol. 281, No. 5384, pp. 1788-1790 (Sep. 18, 1998).
Gates, et al., "Photonic Crystals that can be Addressed with an External Magnetic Field". Adv Mater, vol. 13, No. 21, pp. 1605-1608 (2001).
Gelfi, C., et al., "Investigation of the Properties of Novel Acrylamido Monomers by Capilary Zone Electrophoresis", Journal of Chromatography, vol. 608, pp. 333-341 (1992).
Gerlach. Human Lymphocyte Antigen Molecular Typing. Archives of Pathology & Laboratory Medicine. vol. 126, pp. 281-284 (2002).
Ghazaly, et al., "Synthesis and Characterization of a Macromonomer Crosslinker". Journal of Applied Polymer Science, vol. 77, pp. 1362-1368 (2000).
Ghosh et al. "Covalent attachement of oligonucleotides to solid supports". Nucleic Acids Research. vol. 16, No. 13; pp. 5363-5371 (1987).
Ghosh, P., et al., "A Simple Lithographic Approach for Preparing Patterned, Micron-Scale Corrals for Controlling Cell Growth". Angew. Chem. Int. Ed., vol. 38, No. 11, pp. 1592-1595 (1999).
Giersig et al. Formation of ordered two-dimensional gold colloid lattices by electrophoretic deposition. J. Phys. Chem., vol. 97: 6334-6336 (Apr. 29, 1993).
Giorgi, R., et al., "Nanotechnologies for Conservation of Cultural Heritage: Paper and Canvas Deacidification". Langmuir, vol. 18, pp. 8198-8203 (2002).
Good, L., et al., "Bactericidal antisense effects of peptide-DNA conjugates". Nature Biotechnology, vol. 19, pp. 360-364 (2001).
Goodey et al., "Development of multianalyte sensor arrays composed of chemically derivatized polymeric microspheres localized in micromachined cavitites". Journal of American Chemical Society, vol. 123, pp. 2559-2570 (2001).
Graf et al., "A general method to coat colloidal particles with silica". Langmuir, vol. 19, pp. 6693-6700 (2003).
Grazia et al. In-vivo biomedical monitoring by fiber-optic system. Journal of Lightwave Technology. 13, 1396-1406 (1995).
Yellen, et al., "Statistical Analysis of Weakest Link in Chains of Magnetic Particle Carriers for Applications in Printing Biochemical Arrays". European Cells and Materials, vol. 3, pp. 88-91 (2002).
Grondahl, et al., "Encoding Combinatorial Libraries: A Novel Application of Fluorescent Silica Colloids". Langmuir, vol. 16, No. 25, pp. 9709-9715 (2000).
Gruttner, et al., "New types of silica-fortified magnetic nanoparticles as tools for molecular biology applications". Journal of Magnetism and Magnetic Materials, vol. 94, pp. 8-15 (1999),
Gubin et al., "Identification of the Dombrock blood group glycoprotein as a polymorphic member of the ADP-ribosyltransferase gene family", Blood, Oct. 1, 2000, vol. 96, No. 7, pp. 2621-2627.
Gullberg, M., et al., "Cytokine detection by antibody-based proximity ligation". PNAS, vol. 101, No. 22, pp. 8420-8424 (Jun. 2004).

(56) References Cited

OTHER PUBLICATIONS

Guo, Zhen et al. "Oligonucleotide arrays for high-throughput SNPs detection in the MHC class I genes: HLA-B as a model system". Genome Research; vol. 12, No. 3, pp. 447-457 (Mar. 2002).

Guo, Zhen, "Direct fluorescence analysis of genetic polymorphisms . . . oligonucleotide arrays on glass supports". Nucleic Acids Research, Jul. 1994, Oxford Univ Press, pp. 5456-5465.

Gupta et al. ("Hydrogels: from controlled release to pH-responsive drug delivery" Drug Discov Today. May 15, 2002;7(10):569-79.

Gustafsdottir, S. M., "In vitro analysis of DNA—protein interactions by proximity ligation". PNAS, vol. 104, No. 9, pp. 3067-3072 (Feb. 2007).

Haab et al. Single Molecule Fluorescence Burst Detection of DNA Fragments Separated by Capillary Electrophoresis. Analytical Chemistry, vol. 67 (No. 18) : 3253-3256 (1995).

Hacis et al., "Resequencing and mutational analysis using oligonucleotide microarrays", Nature America; 21 : 42-47 (1999).

Hakala, H., et al. "Simultaneous detection of several oligonucleotides by time-resolved fluorometry: the use of a mixture of categorized microparticles in a sandwich type mixed-phase hybridization assay". Nucleic Acids Research, vol. 26, pp. 5581-5585 (1998).

Hashimi et al., "A Flexible Array format for large-scale, rapid blood group DNA typing". Transfusion, Published Online Apr. 6, 2004, vol. 45, Issue 5, pp. 680-688 (May 2005).

Hashmi, G., et al, "Determination of 24 minor red blood cell antigens for more than 2000 blood donors by high-throughput DNA analysis". Transfusion, vol. 47, No. 4, pp. 736-747 (Apr. 2007).

Zaer, Farid, et al., "Antibody Screening by Enzyme-Linked Immunosorbent Assay Using Pooled Soluble HLA in Renal Transplant Candidates". Transplantation, vol. 63, No. 1, pp. 48-51 (Jan. 15, 1997).

Heinrich, et al., "Interleukin-6-type Cytokine Signaling through the gp 130/Jak/STAT pathway". Biochem J, vol. 334, pp. 297-314 (1998).

Helgesen, et al., "Aggregation of magnetic microspheres: experiements and simulations". Physical Review Letters, vol. 61, No. 15, pp. 1736-1739 (1998).

Helmuth, R., et al., "HLA-DQ Allele and Genotype Frequencies in Various Human Populations, Determined by Using Enzymatic Amplification and Oligonucleotide Probes". Am. J. Hum. Genet, vol. 47, pp. 515-523 (1990).

Hermanson, G. T., "Nucleic Acid and Oligonucleotide Modification and Conjugation". Bioconjugate Techniques, Academic Press, Chapter 17, pp. 639-671 (Jan. 15, 1996).

Yershov et al., "DNA analysis and diagnostics on oligonulceotide microchips". Proceedings of the National Academy of Sciences of the United States of America, vol. 93, No. 10, pp. 4913-4918 (May 14, 1996).

Hiller, J., et al., "Reversibly erasable nanoporous anti-reflection coatings from polyelectrolyte multilayers". Nature Materials, vol. 1, pp. 59-63 (Sep. 2002).

Hirata, H., et al., "Caspases Are Activated in a Branched Protease Cascade and Control Distinct Downstream Processes in Fas-induced Apoptosis". J, Exp. Med., vol. 187, No. 4, pp. 587-600 (1998).

Hizume, et al., "Tandem repeat DNA localizing on the proximal DAPI bands of chromosomes in Larix, pinaceae". Genome, vol. 45, pp. 777-783 (2002).

Holtz, J., et al., "Intelligent Polymerized Crystalline Colloidal Array: Novel Sensor Materials", Analytical Chemistry, vol. 70, No. 4, pp. 780-791 (1998).

Houghton. "General method for the rapid solid-phase synthesis of large numbers of peptides: specificity of anitgen-antibody interaction at the level of individual amino acids". Proc. Natl. Avad. Sci. USA. vol. 82:5131-5135 (1985).

Huff et al., "Technical Milestone: Development of the Logical Observation Identifier Names and Codes (LOINC) Vocabulary". JAIMA, vol. 5, pp. 276-292 (1998).

Iannone, Marie A., et al., "Multiplexed Single Nucelotide Polymorphism Genotyping by Oligonucleotide Ligation and Flow Cytometry". Cytometry, vol. 39, Issue 2, pp. 131-140 (Feb. 17, 2000).

Ide et al., "Synthesis and damage specificity of a novel probe for the detection of abasic sites in DNAa". Biochemistry. vol. 32: 8276-8283 (1993).

Ito, Y., et al., "Patterned Immobilization of Thermoresponsive Polymer", Langmuir, vol. 13, pp. 2756-2759 (1997).

Iwayama, et al., "Optically Tunable Gelled Photonic Crystal Covering Almost the Entire Visible Light Wavelength Region", Langmuir (2002).

Jackman, R. J., et al., "Using Elastomeric Membranes as Dry Resists and for Dry Lift-Off", Langmuir, vol. 15, pp. 2973-2984 (1999).

Jeon, N. L., et al., "Patterned polymer growth on silicon surfaces using microcontact printing and surface-initiated polymerization", Applied Physics Letters, vol. 75, No. 26, pp. 4201-4203 (1999).

John C. Guatelli et al., "Isothermal, in vitro amplification of nucleic acids by a multienzyme reaction modeled after retroviral replication, "Proc. Nat'l Academy of Science USA, vol. 87: pp. 1874-1878 (1990).

Johnson, K. L., et al., "Surface Energy and the Contact of Elastic Solids". Proceedings of the Royal Society of London, Series A, Mathematical and Physical Sciences, vol. 324, No. 1558, pp. 301-313 (Sep. 8, 1971).

Jones et al., "Constraint, Optimization, and Hierarchy: Reviewing Stereoscopic Correspondence of Complex Features". Computer Vision and Image Understanding, vol. 65, No. 1, pp. 57-78 (1997).

Jones et al., "Dielectrophoretic liquid actuation and nanodroplet formation", Journal of Applied Physics, vol. 89, No. 2, pp. 1441-1448 (Jan. 15, 2001).

Kakabakos et al. "Immobilization of Immunoglobulins onto Surface-treated and Untreated Polystyrene Beads for Radioimmunoassays" Clin. Chem. 36 (1990), 492-496.

Kalinina, O., et al., "A core-shell Approach to Producing 3D Polymer Nanocomposites", Macromolecules, vol. 32, pp. 4122-4129 (1999).

Kamholz, et al., "Optical measurement of transverse molecular diffusion in a microchannel". Biophysical Journal, vol. 80, pp. 1967-1972 (2001).

Kamm, R. C., et al. "Nucleic Acid Concentrations in Normal Human Plasma". Clinical Chemistry, vol. 18, pp. 519-522 (1972).

Kandimalla et al., "Cyclicons" as Hybridization-Based Fluorescent Primer-Probes: Bioorganic & Medicinal Chemistry 8 (2000) 1911 to 1916.

Kelly, J.J., et al., "Radical-generating coordination complexes as tools for rapid and effective fragmentation and fluorescent labeling of nucleic acids for microchip hybridization". Analytical Biochemisty, vol. 311, No. 2, pp. 103-118 (Dec. 15, 2002).

Klintschar, et al., "Genetic variation at the STR loci D12S391 and CSF1PO in four populations from Austria, Italy, Egypt and Yemen". Forensic Sci. Int. vol. 97:37-45 (1998).

Kim, E., et al., "Polymer microstructures formed by moulding in capillaries", Nature, vol. 376, pp. 581-584 (1995).

Knipper, et al., Accession No. AF221125.1.1 on Electronic Database at NCBI (Feb. 16, 2000).

Koch et al., "PNA-Peptide Chimerae". Tetrahedron Letters, vol. 36, pp. 6933-6936 (1995).

Koh, et al., "Molding of Hydrogel Microstructures to Create Multiphenotype Cell Microarrays". Analytical Chemistry (2003).

Koh, et al., "Poly(ethylene glycol) Hydrogel Microstructures Encapsulating Living Cells". Langmuir, vol. 18, pp. 2459-2462 (2002).

Kolch. "Meaningful Relationships: The Regulation of the Ras/Raf/MEK/ERK pathway by protein interactions". Biochem J, vol. 351, pp. 289-305 (2000).

Kotov, N., et al., "Layer-by-Layer Self-Assembly of Polyelectrolyte-Semiconductor Nanoparticle Composite Films". J. Phy Chem, vol. 99, pp. 13065-13069 (1995).

Krausa et al. "A Comprehensive PCR-ssP typing system for identification of HLA-A locus alleles", Tissue Antigens, 47 (3) : 237-244 (1996).

Krsko, P., et al., "Electron-Beam Surface Patterned Poly(ethylene glycol) Microhydrogels". Langmuir, vol. 19, pp. 5618-5625 (2003).

Krutzik P.O. et al., "Fluorescent cell barcoding in flow cytometry allows high-throughput drug screening and signal profiling". Nature Methods, vol. 3, No. 5, pp. 361-368 (2006).

(56) References Cited

OTHER PUBLICATIONS

Kubo et al., "A Novel Sensitive and specific assay for abasic sites, the most commonly produced DNA lesion". Biochemistry, vol. 13:3703-3708 (1992).
Kumacheva, E., et al., "Three-dimensional Arrays in Polymer Nanocompositites", Advanced Materials, vol. 11, No. 3, pp. 231-234 (1999).
Kurita-Ochiai, T., et al., "Butyric Acid-Induced T-Cell Apoptosis is Mediated by Caspase-8 and -9 Activation in a Fas-Independent Manner". Clinical and Diagnostic Laboratory Immunology, vol. 8, No. 2, pp. 325-332 (2001).
Vorlop, K. D., et al., "Entrapment of Microbial Cells within Polyurethane Hydrogel Beads with the Advantage of Low Toxicity", Biotechnology Techniques, vol. 6, No. 6, pp. 483-488 (1992).
Kwoh et al., "Transcription based amplification system and detection of amplified human immunodeficiency virus type 1 with a bead-based sandwich hybridization format". Proc. Natl. Acad. Sci, vol. 86, pp. 1173-1177 (Feb. 1989).
LaForge, K. S., et al., "Detection of Single Nucleotide Polymorphisms of the Human Mu Opioid Receptor Gene by Hybridization of Single Nucleotide Extension on Custom Oligonucleotide Gelpad Microchips: Potential in Studies of Addiction". American Journal of Medical Genetics (Neuropsychiatric Genetics), vol. 96, pp. 604-615 (2000).
Lagerholm et al., "Theory for Ligand Rebinding at Cell Membrane Surfaces," Biophysical Journal (1998), vol. 74, pp. 1215-1228.
Lamb, D. J., et al., "Modification of Natural and Artificial Polymer Colloids by Topology-Controlled Emulsion Polymerization". Biomacromolecules, vol. 2, No. 2, pp. 518-525 (2001).
Lander, E. S. "The New Genomics: Global Views of Biology". Sciences, vol. 274, No. 5287, pp. 536-539 (Oct. 25, 1996).
Lander, E. S., et al., "Array of Hope". Nature Genetics Supplement, Perspective, vol. 21, pp. 3-4, (Jan. 1999).
Latour, P., et al., "Polymorphic Short Tandem Repeats for Diagnosis of the Charot-Marie-Tooth IA Duplication". Clinical Chemistry, vol. 47, pp. 829-837 (2001).
Lau, F. Y., et al., "Provision of phenotype-matched blood units: no need for pre-transfusion antibody screening", Haematologica, vol. 86, No. 7, Jul. 2001, pp. 742-748.
Lee et al. "Quantitation of residual WBCs in filtered blood components by high-throughput, real time kinetic PCR", Blood Components, transfusion, vol. 42, pp. 87-93 (Jan. 2002).
Lee, et al., "Combination of Insulin-like Growth FActor (IGF)-1 and IGF-Binding Protein-1 Promotes Fibroblast-Embedded Collagen Gel Contraction". Endocrinology, vol. 137, pp. 5278-5283 (1996).
Lee, H. J., et al., "Fabricating RNA Microarrays with RNA-DNA Surface Ligation Chemistry". Analytical Chemistry, vol. 77, No. 23, pp. 7832-7837 (Dec. 1, 2005).
Lee, S., et al., "Control of Core-Shell Latex Morphology". Polymer Latexes, ACS Symposium, American Chemical Society, pp. 234-253 (1992).
Lemieux: "high throughput single nucleotide polymorphism genotyping technology" Current Genomics. vol. 1:301-311 (2000).
Lhomme et al. "Abasic DNA structure, reactivity and recognition". Biopolymers. vol. 52 : 65-83 (1999).
Li, A., et al., "Multiplexed analysis of polymorphisms in the HLA gene complex using bead array chips". Tissue Anitigens, vol. 63, pp. 518-528 (2004).
Liang L., et al., "Preparation of Composite-Crosslinked Poly(N-isopropylacrylamide) Gel Layer and Characteristics of Reverse Hydrophilic-Hydrophobic Surface", Journal of Applied Polymer Science, vol. 72, pp. 1-11 (1999).
Liang, L., et al., "Temperature-sensitive membranes prepared by UV photopolymerization of N-isoproprylacrylamide on a surface of porous hydrophilic polypropylene membranes", Journal of Membrane Science, vol. 162, pp. 235-246 (1999).
Liebert, M. R., et al., "Dynamics of the holes in human erythrocyte membrane ghosts". J. Biological Chemistry, vol. 257, No. 19, pp. 11660-11666 (1982).
Lin et al. "Raman Studies of Bovine Serum Albumin" . Biopolymers 15:203-218 (1976).
Lindahl et al., "Rate of depuriniation of native deoxyribonucleic acid". Biochemistry. vol. 11, No. 19: 3610-1617 (1972).
Lindahl et al., "Rate of chain breakage at apurinic sites in double-stranded deoxyribonclueic acid" Biochemistry, vol. 11, No. 19:3618-3623 (1972).
Lipshutz, R. J., et al., "High Density Synthetic Oligonucleotide Arrays". vol. 21, pp. 20-24 (Jan. 1999).
Liu, et al., "Development of a Carbon Dioxide-Base Microencapsulation Technique for Aqueous and Ethanol-Based Latexes". Langmuir (2002).
Liu, V, et al, "Three-Dimensional Photopatterning of Hydrogels Containing Living Cell". Biomedical Microdevices, vol. 4, No. 4, pp. 257-266 (2002).
Lofas, et al., "Methods for site controlled coupling to carboxymethyldextran surfaces in surface plasmon resonance sensors". Biosensors & Bioelectronics, vol. 10, pp. 813-822 (1995).
Loomans, E., et al., "Assessment of the functional affinity constant of monoclonal antibodies using an improved enzyme-linked immunosorbent assay". Journal of Immunological Methods, vol. 184, pp. 207-217 (1995).
Ye et al., "Fluorescent Microsphere-Based Readout Technology for Multiplexed Human Single Nucleotide Polymorphism Analysis and Bacterial Identification" Human Mutation, Apr. 17, 2001 (4); 305-16).
Lund et al. Assessment of Methods for Covalent Bonding of Nucleic Acids to Magnetic Beads, Bynabeads, and the Characteristics of the Bound Nucleic Acids in Hybridization Reactions, Nucleic Acids REsearch vol. 16, No. 22, 10861-10880 (1988).
Luo et al., "Emulsion Copolymerization of Butyl Acrylate with Cationic Monomer Using Interfacial Redox Initiator System". Journal of Polymer Science, vol. 39, pp. 2696-2709 (2001).
Lvov, Y, et al., "Alernate Assembly of Ordered Multilayers of SiO2 and Other Nanoparticles and Polyions". Langmuir, vol. 13, pp. 6195-6203 (1997).
MacBeath et al., "Printing proteins as microarrays for high-throughput function determination". Science, vol. 289; pp. 1760-1763 (Sep. 8, 2000).
Maldonado-Rodriguez et al., "Hybridization of glass-tethered oligonucleotide probes to . . . ", Molecular Biotechnology, vol. 11, No. 1, pp. 1-12 (1999).
Marras et al., Multiplex detection of single-nucleotide variations using molecular beacons: Genetic Analysis: Biomolecular Engineering 14 (1999) 151-156.
Marsh, S. G. E., et al., The HLA Facts Book, "HLA Typing at the DNA Level", Academic Press, Chapter 6, pp. 37-39 (2000).
Martin, M., et al. "A Method for Using Serum or Plasma as a Source of DNA for HLA Typing". Human Immunology, vol. 33, pp. 108-113 (1992).
Martinell, J. et al., "Three mouse models of human thalassemia", Proc. Natl. Acad. Sci, USA. Aug. 1981, vol. 78, No. 8, pp. 5056-5060 (see especially p. 5057, col. 1, last paragraph, Figure 4, and the legend to Figure 4.
Maskos, U. et al., "Parallel analysis of oligodeoxyribonucleotide (oligonucleotide) interactions. I. Analysis of factors influencing oligonucleotide duplex formation". Nucleic Acids Research, vol. 20, No. 7, pp. 1675-1678 (1992).
Maskos, U., et al., "Oligonucleotide hybridisations on glass supports: a novel linker for oligonucleoptide synthesis and hybridisation properties of oligonucleotides synthesized in situ". Nucleic Acids Research, vol. 20, No. 7, pp. 1679-1684 (1992).
Matthews et al., "Biochemistry: A Short Course". New York: John Wiley & Sons, Inc, p. 25(1997).
Maxam et al., "A new method for sequencing DNA," Proc. Natl. Acad. Sci. USA. vol. 74, No. 2, pp. 560-564, Feb. 1977.
McCloskey, et al., "Magnetic Cell Separation: Characterization of Magnetophoretic Mobility". Anal. Chem., vol. 75, pp. 6868-6874 (2003).
McCloskey, et al., "Magnetophoretic Mobilities Correlate to Antibody Binidng Capacities". Cytometry, vol. 40, pp. 307-315 (2000).

(56) References Cited

OTHER PUBLICATIONS

Mei et al. "Genome-wide Detection of Allelic Imbalance Using Human SNPs and High-Density DNA Arrays". Genome Research. vol. 10, pp. 1126-1137 (2000).
Michael, et al., "Randomly ordered addressable high-density optical ssensor arrays". Anal. Chem, vol. 70, pp. 1242-1248 (1999).
Micheletto et al., "A simple method for the production of a two-dimensional ordered array of small latex particles". Langmuir, vol. 11, pp. 3333-3336 (1995).
Moller, E., et al., "The Use of Magnetic Beads Coated with Soluble HLA Class I or Class II Proteins in Antibody Screening and for Specificity Determination of Donor-Reactive Antibodies". Transplantation, vol. 61, No. 10, pp. 1539-1545 (May 27, 1996).
Moore, et al., "The use of magnetite-doped polymeric microspheres in calibrating cell tracking velocimetry". J. Biochem. Biophys. Methods, vol. 44, pp. 115-130 (2000).
Morag et al. "Immobilized nitro-avidin and nitro-streptavidin as reusable affinity matrices for application in avidin-biotin technology". Analytical Biochemistry. vol. 243: 257-263 (1996).
Mori, et al., Computer program to predict liklihood of finding an HLA-matched donor: Methodology, validation, and application. Biology of Blood and Marrow Transplantation, vol. 2, pp. 134-144 (1996).
Morishima et al., "Microflow system and transportation of DNA molecule by dielectrophoretic force utilizing the conformational transition in the higher order structure of DNA molecule". Proceedings—IEEE Annual International Workshop on Micro Electro Mechanical Systems: An investigation of micro structures, sensors, actuators, machines and robots. Nagoya, Jan. 26-30, 1997.
Muller et al., "Gene and Haplotype Frequencies for the Loci HLA-A, HLB-B, and HLA-DR Based on Over 13,000 German Blood Donors". Human Immunology, 2003, 64: 137-151.
Mullis et al. Specific Synthesis of DNA in Vitro via a Polymerase-Catalyzed Chain Reaction Methods in Enzymology, 1987; vol. 155, pp. 335-350.
Nagarajan et al., "Identifying Spots in Microarray Images", IEEE Transactions on Nanobioscience, vol. 1, No. 2, pp. 78-84 (Jun. 2002).
Nagayama et al., "Fabrication of two-dimensional colloidal arrays". Phase Transitions, vol. 45, 185-203 (1993).
Nam, J., et a., "Colorimetric Bio-Barcode Amplification Assay for Cytokines". Anal. Chem., vol. 77, pp. 6985-6988 (2005).
Nau et al., "A Command Processor for the Determination of Specificities fro Matrices of Reactions Between Blood Cells and Antisera". Computers and Biomedical Research, vol. 10, pp. 259-269 (1977).
Nazarenko et al. (2002) Multiplexed quantitiative PCR using self-quenched primers labeled with a single fluorophore. Nucleic Acids Research, 30 (9), e37.
Niemeyer et al., "DNA-directed Immobilization: Efficient, Reversible, and Site-Selective Surface Binding of Proteins by means of Covalent Stretavidin Conjugates". Analytical Biochemistry, vol. 268, pp. 54-63 (1999).
Niemeyer et al., "Oligonucleotide-directed self-assembly of proteins: semisynthetic DNA—streptavidin hybrid molecules as connectors for the generation of macroscopic arrays and the construction of supramolecular bioconjugates". Nucleic Acids Research, vol. 22, pp. 5530-5539 (1994).
Nygren, "Molecular Diagnostics of Infectious Diseases" Royal Institute of Technology Department of Biotechnology, Stockholm 2000, pp. 1-68.
Ohlmeyer, M. H. J. et al. "Complex Synthetic Chemical Libraries Indexed with Molecular Tags". Proceedings of the National Academy of Sciences, USA, National Academy of Science, Washington DC. vol. 90, Dec. 1, 1993, pp. 10922-10926.
Okubo, and Yamashita. "Thermodynamics for the preparation of micorn-sized, monodispersed highly monomer-'absorbed' polymer particles utilizing the dynamic swelling method." Colloids and Surfaces, 1999:153-159.

Okubo et al., "Preparation of micron-size monodisperse polymer particles by seeded polymerization utilizing the dynamic monomer swelling method". Colloid and Polymer Science, vol. 269, No. 3, pp. 222-226 (1991).
Olejnik et al., "Photocleavable biotin phosphoramidite for 5'-end-labeling, purification & phosphorylation of oligonucleotides", Nucleic Acids Research 1996, vol. 24, 2:361-366.
Oliver, D., et al, "Use of Single Nucleotide Polymorphisms (SNP) and Real-Time Polymerase Chain Reaction for Bone Marrow Engraftment Analysis". Journal of Molecular Diagnostics, vol. 2, No. 4, pp. 202-208 (Nov. 2000).
Olson et al. "A common langauage for physical mapping of the human genome". Science, vol. 245, pp. 1434-1435 (1989).
Otero, T. F., et al., "Electrochemically initiated acrylic acid/acrylamide copolymerization", J. Electroanal. Chem., vol. 256, pp. 433-439 (1998).
Otero, T. F., et al., "Electroinitiated polymerization of acrylamide in DMG: Attempts at an interfacial model", J. Electroanal. Chem., vol. 304, pp. 153-170 (1991).
Pastinen, et al., "A System for specific, high-throughput genotyping by allele-specific primer extension on microarrays". Genome Res., vol. 10, pp. 1031-1042 (2000).
Peter, C., et al., "Optical DNA-sensor chip for real-time detection of hybridization events". Fresenius J. Anal. Chem, vol. 371, pp. 120-127 (Jun. 2001); Published online Springer-Verlay 2001.
Wilson, M. R., et al., "A New Microsphere-based Immunofluorescence Assay for Antibodies to Membrane-associated Antigens". Journal of Immunological Methods, vol. 107, pp. 231-237 (1988).
Peterson, et al. "Fiber Optic pH probe for physiological use". Anal. Chem. vol. 52, 864-869 (1980).
Peterson, et al., "Fiber Optic Sensors for Biomedical Applications". Science, vol. 13; pp. 123-127 (1984).
Peytavi et al., "Correlation between microarray DNA hybridization efficiency and the position of short capture probe on the target nucleic acid". Biotechniques, vol. 39, No. 1, pp. 89-96 (2005).
Pooga, M., et al., "Cell-Penetrating constructs regulate galanin receptor levels and modify pain transmission in vivo" Nature Biotechnology, vol. 16, pp. 857-861 (1998).
Pope. "Fiber optic chemical microsensors employing optically active silica microspheres". SPIE, vol. 2388; pp. 245-256 (1995).
Prati D. et al., DNA Enzyme Immunoassay of the PCR-Amplified HLA-DQ Alpha Gene for Estimating Residual Leukocytes in Filtered Blood Clincial and Diagnostic Laboratory Immunology, Mar. 1995, p. 182-185.
Pregibon et al, "Magnetically and Biologically Active Bead-Patterned Hydrogels". Langmuir, vol. 22, pp. 5122-5128 (2006).
Preza, "Phase Estimation using rotational diversity for differential interference contrast microscopy". Dissertation presented to the Washington University, Server Institute of Technology, Department of Electrical Engineering; St. Louis, MO (Aug. 1998).
Proudinikov et al., "Chemical methods of DNA and RNA fluorescent labeling". Nucleic Acids Research. vol. 24, No. 22: 4535-4542 (1996).
Proudnikov, D., et al., "Immobilization of DNA in Polyacrimide Gel for the Manufacture of DNA and DNA-Oligonucleotide Microchips", Analytical Biochemistry, vol. 259, pp. 34-41 (1998).
Quon, R., et al., "Measurement of the Deformation and Adhesion of Rough Solids in Contact". J. Phys. Chem., vol. 103, pp. 5320-5327 (1999).
Rabbany et al., "Assessment of hetrogeneity in antibody displacement reactions". Anal Chem, vol. 69, pp. 175-182 (1997).
Radtchecnko et al., "Core-shell structures formed by the solvent-controlled precipitation of luminescent ScTe nanocrystals on latex spheres". Advanced Materials, vol. 13, No. 22, pp. 1684-1687 (2001).
Radtkey et al., "Rapid, high-fidelity analysis of simple sequence repeats on an electronically active DNA microchip". Nucleic Acids Research, vol. 28, No. 7, p. e17 (2000).
Ramsay, G., "DNA Chips: State-of-the-Art". Nature Biotechnology, vol. 16, pp. 40-44 (Jan. 1998).

(56) References Cited

OTHER PUBLICATIONS

Reddy et al., "Determination of the Magnetic Susceptibility of Labeled Particles by Video Imaging". Chemical Engineering Science, vol. 51, No. 6, pp. 947-956 (1996).
Reid M.E., et al., "Novel Dombrock blood group genetic variants . . . ", Blood (ASH Annual Meeting Abstract) 2004, 104: Abstract 383.
Relogio, A. et al., "Optimization of oligonucleotide-based DNA microarrays", Nucl. Acids Res., vol. 30, e51, pp. 1-10 (2002).
Richardson et al., "The use of coated paramagnetic particles as a physical label in a magneto-immunassay". Biosensors & Bioelectronics, vol. 16, pp. 989-993 (2001).
Richardson, et al., "A novel measuring system for the determination of paramagnetic particle lables for use in magneto-immunoassays". Biosensors & Bioelectronics, vol. 16, pp. 1127-1132 (2001).
Richetti et al., "Two-dimensional aggregations and crystallization of a colloidal suspension of latex spjeres", J. Physique Letter. vol. 45, pp. L-1137 to L-1143 (1984).
Righetti, P. G., et al., "Electrophoresis gel media: the state of the art", J. Chromatogr B., Biomed Sci Appl, vol. 699, No. 1-2, pp. 63-75 (Oct. 10, 1997).
Roberts et al. "Patterned magnetic bar array for high-thoughput DNA detection" IEEE Transaction on Magnetics. vol. 40, No. 4: 3006-3008 (2004).
Rubina et al, "Hydrogel drop microchips with immobilized DNA: properties and methods for large-scale production". Analytical Biochemistry, vol. 325, pp. 92-106 (2004).
Rudzinski, et al., "pH-sensitive acrylic-based copolymeric hydrogels for the controlled release of a pesticide and a micronutrient". Journal of Applied Polymer Science, vol. 87, pp. 394-403 (2003).
Sacchetti, et al. "Efficiency of Two Different Nine-Loci Short Tandem Repeat Systems for DNA Typing Purposes". Clinical Chemistry, vol. 45, No. 2, pp. 178-183 (1999).
Saito, K., et al., "Detection of Human Serum Tumor Necrosis Factor-alpha in Healthy Donors, Using a Highly Sensitive Immuno-PCR Assay". Clinical Chemistry, vol. 45, No. 5, pp. 665-669 (1999).
Sambrook et al., "Precipitation with Ethanol or Isopropanol", Concentrating Nucleic Aicds, Molecular Cloning vol. 3, pp. E3-E4 and E.10-E.15 (1989).
Sano, T, et al., "Immuno-PCR: Very Senisitive Antigen Detection by Means of Specific Antibody-DNA Conjugates". Science, vol. 258, pp. 120-122 (Oct. 2, 1992).
Santa Lucia, J. Jr., "A unified view of polymer, dumbbell, and oligonucleotide DNA nearest-neighbor thermodynamics". PNAS USA, vol. 95, pp. 1460-1465 (1998).
Schaid et al., "Score Tests for Association between traits and Haplotypes when Linkage Phase is Ambiguous", American Journal of Genetics. vol. 70, pp. 425-434 (2002).
Schena et al., "Quantitative Monitoring of Gene Expression Patterns with a Complementary DA Microarray". Science, vol. 270, pp. 467-470 (1995).
Schouten, Jan P., et al., "Relative Quantification of 40 Nucleic Acid Sequences by Multiplex Ligation-Dependent Probe Amplification". Nucleic Acids Research, vol. 30, No. 12, e57 (Jun. 15, 2002).
Schreiber, G. B., et al., "Increasing Blood Availability by changing Donation Patterns". Transfusion, vol. 43, pp. 591-597 (2003).
Schreuder et al., "The HLA Dictionary 1999: A Summary of HLA-A, B, C, DRB1/3/4/5, DOB1 alleles and their association with serologically defined HLA-A, B, C, DR and DQ antigens", Tissue Antigens 54 : 409-437 (1999).
Schumaker, et al., "Mutation Detection by solid phase primer extension", Human Mutation 7:346-354 (1996).
Wilson et al., "A generalized method for magnetite nanoparticle steric stabilization utilizing block copolymers containing carboxylic acids". European Cells and Materials, vol. 2, Suppl 2, pp. 202-209 (2002).
Schuster et al. "Allele-specific and asymetric polymerase chain reacton amplification in combination: a one step polymerase chain protocol for rapid diagnosis of familial defective apolipoprotein B-100", Anal Biochem. Jul. 1992; 204 (1):22-5).

Scillian, James J., et al., "Early Detection of Antibodies Against rDNA-Produced HIV Proteins with a Flow Cytometric Assay". Clinical Chemistry, vol. 40, No. 3, pp. 420-425 (1994).
Scott et al., "Properties of Fluorophores on solid phase resins; Implications for screening, encoding and reaction monitoring". Bioorganic & Medicinal Chemistry Letter, vol. 7, No. 12, pp. 1567-1572 (1997).
S. Dubiley et al., "Polymorphism Analysis and Gene Detection by minsequencing on an array of gel immobilized primers." Nucleic Acids Research, 1999;i-vi. vol. 27, No. 16.
S. Ebel et al. "Very Stable Mismatch Duplexes: Structural and Thermodynamic Studies on G-A Mismatches in DNA" Biochemistry 31:12083-86 (1992).
Seeman, P., et al., "Structure of Membrane Holes in Osmotic and Saponin Hemolysis"; The Journal of Cell Biology, vol. 56; pp. 519-527 (1973).
Sehgal et al. "A method for the high effieiency of water-soluble carbodiimide-mediated amidation". Analytical Biochemistry. vol. 218:87-91 (1994).
Seltsam, et al., Systematic analysis of the ABO gene diversity within exons 6 and 7 by PCR screening reveals new ABO alleles, Transfusion, vol. 43, pp. 428-439 (2003).
Sennerfors, T., et al., "Adsorption of Polyelectrolyte-Nanoparticle Systems on Silica: Influence of Ionic Strength". Journal of Colloid and Interface Science, vol. 254, pp. 222-226 (2002).
Serizawa, T., et al., "Electrostatic Adsorption of Polystyrene Nanospheres onto the Surface of an Ultrathin Polymer Film prepared by Using an Alternate Adsorption Technique". Langmuir, vol. 14, pp. 4088-4094 (1998).
Sethu, P; "Microfluidic diffusive filter for apheresis (leukopheresis)"; Lab Chip, vol. 6, No. 1, pp. 83-89 (Jan. 2006); Published electronically Nov. 11, 2005.
Seul et al., "Domain Shapes and Patterns: The Phenomenology of Modulated Phases", Science, vol. 267:476-483 (1995).
Seul et al., "Scale transformation of magnetic bubble arrays: coupling of topological disorder and polydispersity". Science, vol. 262: 558-560 (1993).
Sgaramella, V., et al., "Total Synthesis of the Structural Gene for an Alanine Transfer RNA from Yeast. Enzymic Joining of the Chemically Synthesized Polydeoxynucleotides to form the DNA Duplex Representing Nucleotide Sequence 1 to 20". J. Mol. Biology, vol. 72, pp. 427-444 (1972).
Sham , P. et al., "Haplotype Association of Discrete and Continuous Traits Using Mixture of Regression Models", Behavior Genetics, Mar. 2004, 34(2), pp. 207-214.
Shevkoplyas, S., et al., "Biomimetic autoseparation of leukocytes from whole blood in a microfluidic device"; American Chemical Society; vol. 77, No. 3, pp. 933-937 (Feb. 1, 2005).
Shon. "Application Note—New Best Practices for Biosample Management: Moving Beyond Freezers". American Biotechnology Laboratory, vol. 23, No. 2, pp. 10-13 (2005).
Shoyer, Terrie W., et al., "A Rapid Flow Cytometry Assay for HLA Antibody Detection Using a Pooled Cell Panel Convering 14 Serological Crossreacting Groups". Transplantation, vol. 59, No. 4, pp. 626-630 (1995).
Siegel, D., "Phage display-based molecular methods in immunohematology". Transfusion, vol. 47, pp. 89S-94S (Jul. 2007 Supplement).
Simon, R. "Application of optimization methods to the hematological support of patients with disseminated malignacies", Mathematical Biosciences, vol. 25, 1975, pp. 125-138.
Skalnik et al., "A Rapid Method for Characterizing transgenic Mice", S. Biotechniques 8:34 (1990).
Skolnick et al. "Simultaneous analysis of multiple polymorphic loci using amplified sequence polymorphisms (ASPs)". Genomics, vol. 2, pp. 273-279 (1988).
Smay, J., et al., "Colloidal Inks for Directed Assembly of 3-D Peridoic Structures". Langmuir, vol. 18, pp. 5429-5437 (2002).
Smith, J. W., et al., "RED: A Red-Cell Antibody Identification Expert Module". Journal of Medical Systems, vol. 9, No. 3, pp. 121-138 (1985).

(56) References Cited

OTHER PUBLICATIONS

Southern E. M., "DNA Fingerprinting by hybridisation to oligonucleotide arrays". Electrophoresis, vol. 16, No. 9, pp. 1539-1542 (1995).
Southern, E. M., et al., "Analyzing and comparing nucleic acid sequences by hybridization to arrays of oligonucleotides: evaluation using experimental models". vol. 13, No. 4, pp. 1008-1017 (Aug. 1992).
St. Louis, M, et al., "The Dombrock blood group system: A Review", Transfusion 43: 1126-1132 (2003).
Steemers, F.J. (2000) Screening unlabeled DNA targets with randomly ordered fiber-optic gene arrays. Nat. Biotechnol., 18, 91-94.
Stemmer, C., et al., "Use of Magnetic Beads for Plasma Cell-free DNA Extraction: Toward Automation of Plasma DNA Analysis for Molecular Diagnostics". Clinical Chemistry, vol. 49, No. 11, pp. 1953-1955 (2003).
Stevens, P. W., et al. "Imaging and Analysis of Immobilized Particle Arrays". Analytical Chemistry. vol. 75, pp. 1147-1154 (2003).
Storry et al, "Genetic Basis of blood group diversity". British Journal of Haematology, vol. 126, pp. 759-771 (2004).
Strobel E., et al., "The molecular basis of Rhesus antigen E", Transfusion 44:407-409 (2004).
Sukhishvilli, S.A. et al. "Adsorption of human serum albumin: Dependence on molecular architecture of the oppositely charged surface" J. Chem. Phys. 110, 10153-10161 (1999).
Sun et al., "Continuous, Flow-Through Immunomagnetic Cell Sorting in a Quadrupole Field". Cytometry, vol. 33, pp. 469-475 (1998).
Suzawa et al., "Adsorption of Plasma Proteins onto Polymer Latices". Advances in Colloid and Interface Science, vol. 35, pp. 139-172 (1991).
Svitel, et al., "Combined Affinity and Rate Constant Distributions of Ligand Populations from Experimental Surface Binding Kinetics and Equilibria". Biophysical Journal, vol. 84, pp. 4062-4077 (Jun. 2003).
Syvanen, "From Gels to Chips: Minisequencing Primer Extensions for Analysis of Pont Mutations and Single Nucelotide Polymorphisms", Human Mutation 13:1-10 (1999).
Syvanen, A., et al., "Identification of Individuals by Analysis of Biallelic DNA Markers, Using PCR and Solid-Phase Minisequencing". Am. J. Hum. Genet, vol. 52, pp. 46-59 (1993).
Syvannen, A. "Toward genome-wide SNP genotyping". Nature Genetics Supplement. vol. 37: s5-s10 (2005).
Sze. MIS Diode and Charge-Coupled Device. The Physics of Semiconductors, Chapter 7, pp. 362-430 (2nd Edition) (1981).
Takeda et al. "Conformational Change of Bovine Serum Albumin by Heat Treatment", J. Protein Chemistry 8:653-659, No. 5 (1989).
Tanaka, T., et al., "Mechanical instability of gels at the phase transition", Nature, vol. 325, pp. 796-798 (1987).
Taniguchi et al. "Adsorption/desorption behavior and covalent grafting of an antibody onto cationic amino-functionalized poly(styrene-N-isoprapylacrylamide) core-shell latex particles". Colloids and Surfaces B: Biointerfaces. vol. 29: 53-65 (2003).
Tarnok et al., "Cytometric Bead Array to Measure Six Cytokines in Twenty-Five Microliters of Serum," Clinical Chemistry, (2003), vol. 49, No. 6, pp. 1000-1002.
Taylor et al., "Linked oligodeoxynucleotides show binding cooperativity and can selectively impair replication of deleted mitochondrial DNA templates", Nucleic Acids Research. vol. 29, No. 16, pp. 3404-3412 (2001).
Tobitani et al. "Heat-induced gelation of globular proteins. 1. Model for the effects of time and temperature onthe gelation time of BSA gels." Macromolecules. vol. 30:4845-4854 (1997).
Tokumasu F. et al., Development and application of quantum dots for immunocytochemistry of human erythrocytes, J. Microscopy, 2003, pp. 256-261, vol. 211, pt. 3.
Tonisson et al., "Arrayed primer extension on the DNA chip; Method and applications", Microarray Biochip Technology, Biotechniques Books, 247-262 (2000).
Tsuchihashi, Z. et al. "Progress in high throughput SNP genotyping methods", The Pharmacogenomics Journal 2:103-110 (Apr. 2002).

Trau et al., "Field-induced layering of colloidal crystal", Science, vol. 272; pp. 706-709 (1996).
Trang D.T.X. et al. "One step concentration of malarial parasite-infected red blood cells and removal of contaminating white blood cells", Malaria Journal (2004) pp. 1-7 from http://www.malariajournal.com/content/3/1/7.
Trau et al., "Nanoencapsulated microcrystalline particles for superamplified biochemical assays", Anal. Chem, vol. 74, No. 21, pp. 5480-5486. Web Release Date: Sep. 25, 2002.
Turcanu et al, "Cell Identification and isolation on the basis of cytokine secretion: A novel tool for investigating immune responses". Nature Medicine, vol. 7, No. 3, pp. 373-376 (Mar. 2001).
Tyagi et al., Molecular Beacons: Probes that Flouresce upon Hybridization, Nature Biotechnology vol. 14, pp. 303-308 (1996).
Vainrub, A., et al., "Sensitive quantitative nucleic acid detection using oligonucleotide microarrays". Journal of the American Chemical Society, vol. 125, No. 26, pp. 7798-7799, (Jun. 2003).
Van Kempen, et al., "Mean and Variance of Ratio Estimators Used in Fluorescence Ratio Imaging". Cytometry, vol. 39, pp. 300-305 (2000).
Van Zoelen, "Receptor-ligan interaction: a new method for determing binding parameters without a priori assumptions on non-specific binding". Biochem J., vol. 262, pp. 549-556 (1989).
Vasiliskov, A. V., et al., "Fabrication of Microarray of Gel-Immobilized Compounds on a Chip by Copolymerization". BioTechniques, vol. 27, pp. 592-606 (Sep. 1999).
Vaynberg et al. "Structure and extent of absorbed gelatin on acrylic latex and polystyrene collodial particles". Journal of Colloid and Interface Science. vol. 205:131-140 (1998).
Vet, J.A.M. (1999) Multiplex detection of four pathogenic retroviruses using molecular beacon. Proc. Natl. Acad. Sci. USA, 96, 6394-6399.
Vilain. "CYPs, SNPs, and Molecular Diagnosis in the Postgenomic Era". Clinical Chemistry, vol. 44, pp. 2403-2404 (1998).
Wahl et al., "Efficient transfer of large DNA fragments from agarose gels to diazobenzyloxymethyl-paper and rapid hybridization by using dextran sulfate". Proc. Natl. Acad. Sci. USA. vol. 76, No. 8: 3583-3687 (1979).
Wang, D., et al, "Large-Scale Identification, Mapping, and Genotyping of Single-Nucleotide Polymorphisms in the Human Genome". Science, vol. 280, No. 5366, pp. 1077-1082 (May 15, 1998).
Warren, J. A., "Selected Spacings During Directional Solidification of a Binary Alloy", Spatio-Temporal Patterns, Ed. P. E., Cladis and P. Palffy-Muhoray, SFI Studies in the Science of Complexity, Addison-Wesley, pp. 91-105 (1995).
Weinfeld et al., "Selective hydrolysis by exo- and endonucleases of phosphodiester bonds adjacent to an apurinic site". Nucleic Acids Research, vol. 17, No. 10: 3735-3744 (1989).
Weissenbach et al. "A Second generation linkage map of the human genome". Nature, vol. 359, pp. 794-801 (1992).
Wen, et al., "Planar Magnetic Colloidal Crystals". Physical Review Letters, vol. 85, No. 25, pp. 5464-5467 (2000).
Wiedmann, M., et al., Ligase Chain Reaction (LCR)—Overview and Applications, PCR Methods and Applications, Genome Research, vol. 3, pp. s51-s64 (1994).
Yeang et. al. Molecular classification of multiple tumor types. Bioinformatics vol. 17 Suppl. 1, pp. s316-s322 (2001).
J.F. Chapman et al., "Working Party of the BCSH: Guidelines for compatibility procedures in blood transfusion laboratories", Transfusion Medicine, vol. 14, pp. 59-73 (2004).
Yamashita et al., "Thermodynamics for the preparation of micronsized, monodispersed highly monomer absorbed polymer particles utilizing the dynamic selling method". Colloids and Surfaces, vol. 153, pp. 153-159 (1999).
Yao et al., "Molecular-beacon-based array for sensitive DNA analysis". Analytical Biochemistry, vol. 331, pp. 216-223 (2004).
Fukuda et al., "Noncontact manipulation of DNA molecule 1. Transportation of DNA molecule by dielectric force". Nippon Kikai Gakkai Ronbunshu, vol. 62: 2765-2772 (1996).
Hermanson, Greg T., "Zero Length Cross-Linkers"; Bioconjugate Techniques; Academic Press, pp. 170-176 (1996).

(56) References Cited

OTHER PUBLICATIONS

Hermanson, Greg T., "Bioconjugate Techniques", Bioconjugate Techniques; Academic Press, San Diego, 430-33, (1996).

MacBeath et al., "Printing proteins as microarrays for high-throughput function determination," Science vol. 289: 1760-1763 (2000).

Tobitani et al. "Heat-induced gelation of globular proteins 2. Effect of environmental factors on single-component and mixed-protein gels," Macromolecules; vol. 30: 4855-4862 (1997).

Wittemann et al., "Interaction of Proteins with Spherical Polyelectrolyte Brushes" (Polyer Institute, University of Karisruhe, Karisruhe, Germany) Poster Oct. 2001.

* cited by examiner

Peptide Encoding Strategy for Different Peptides

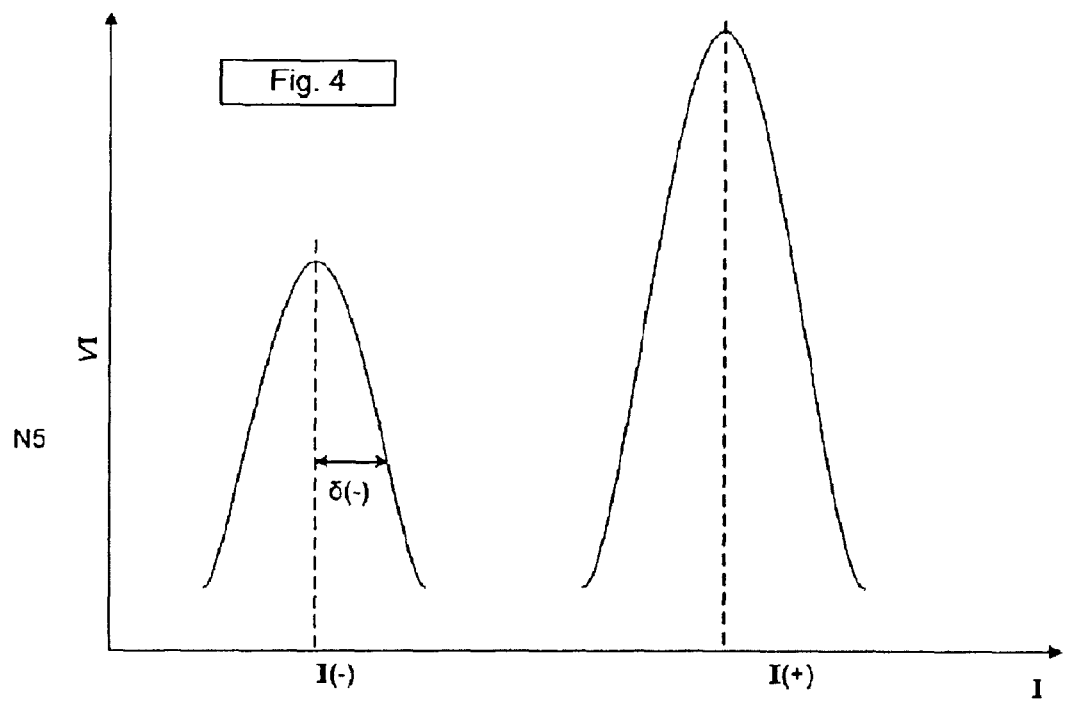
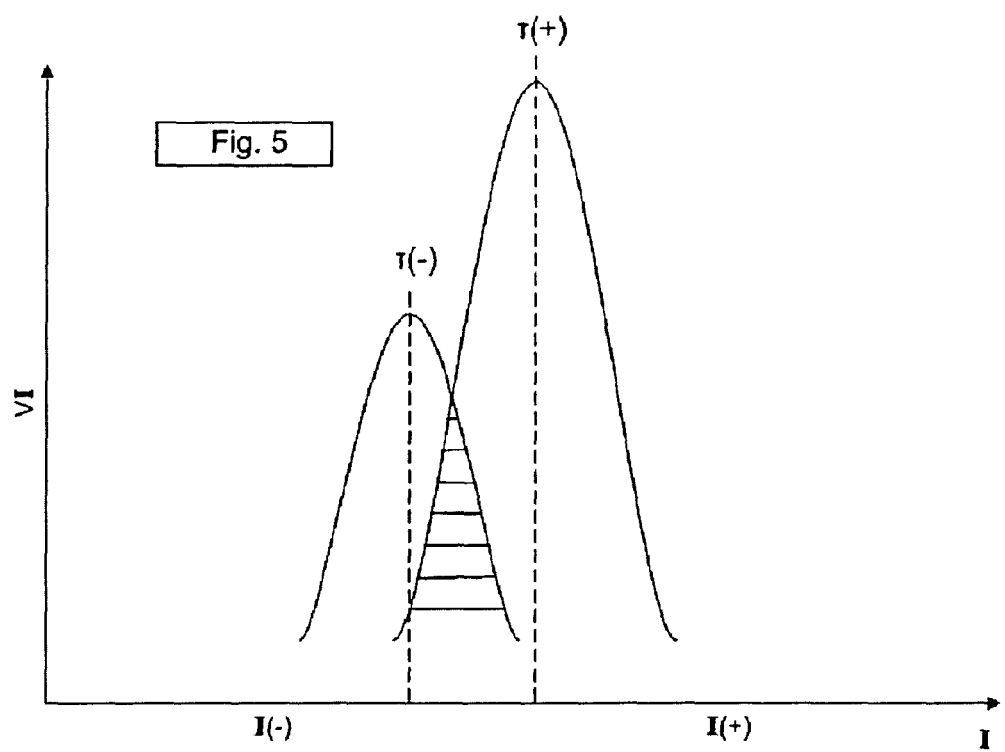

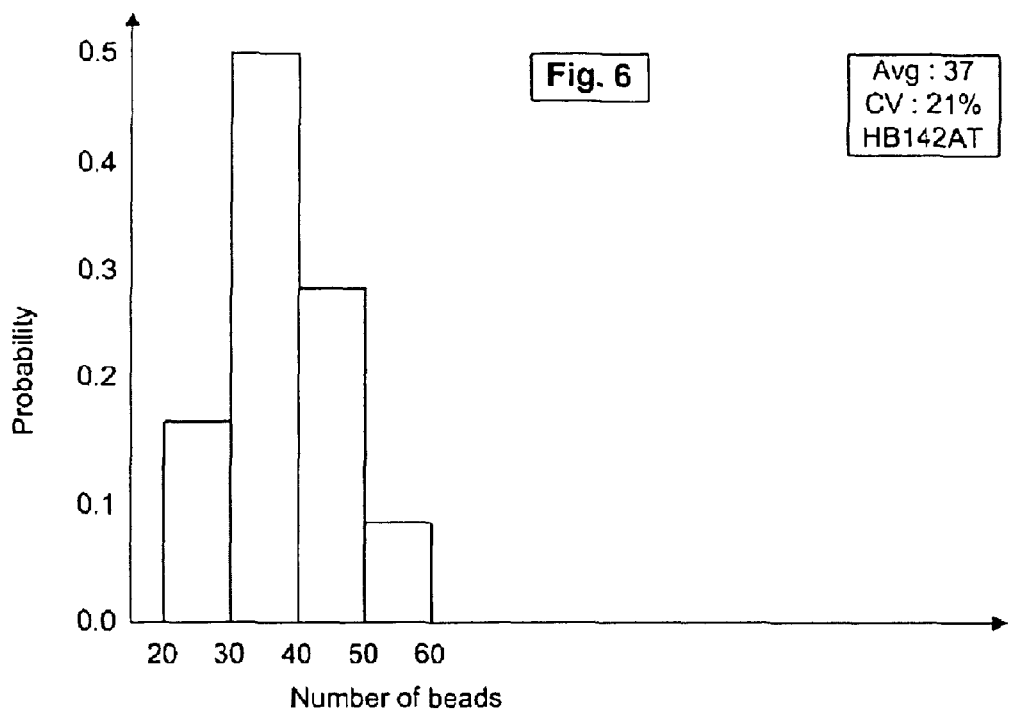
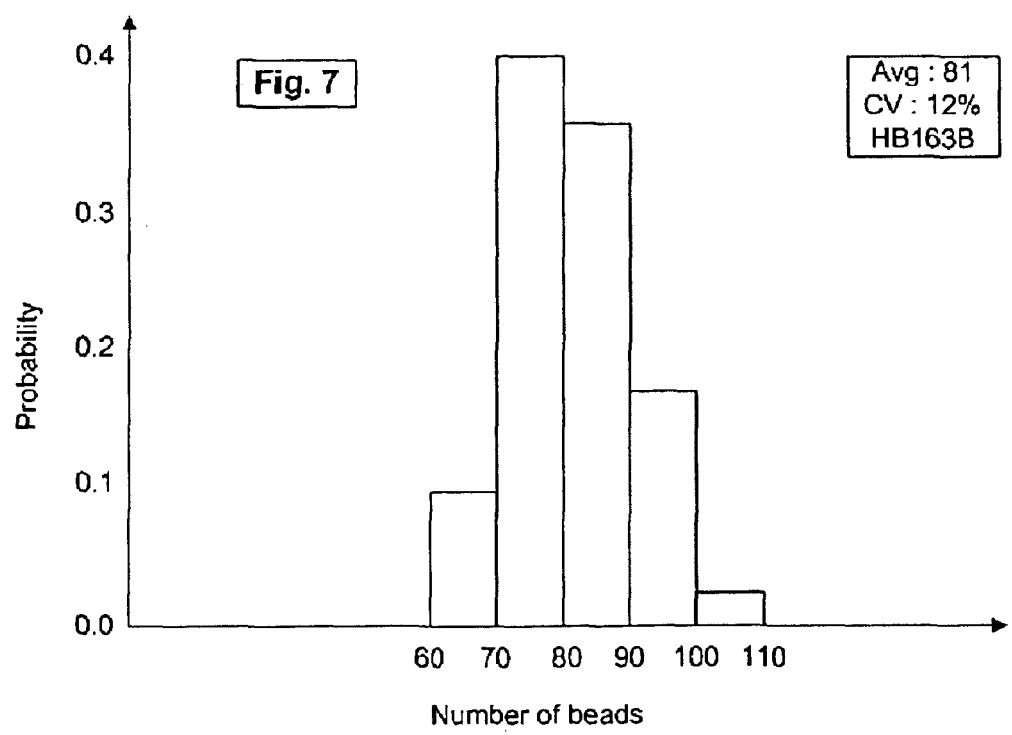

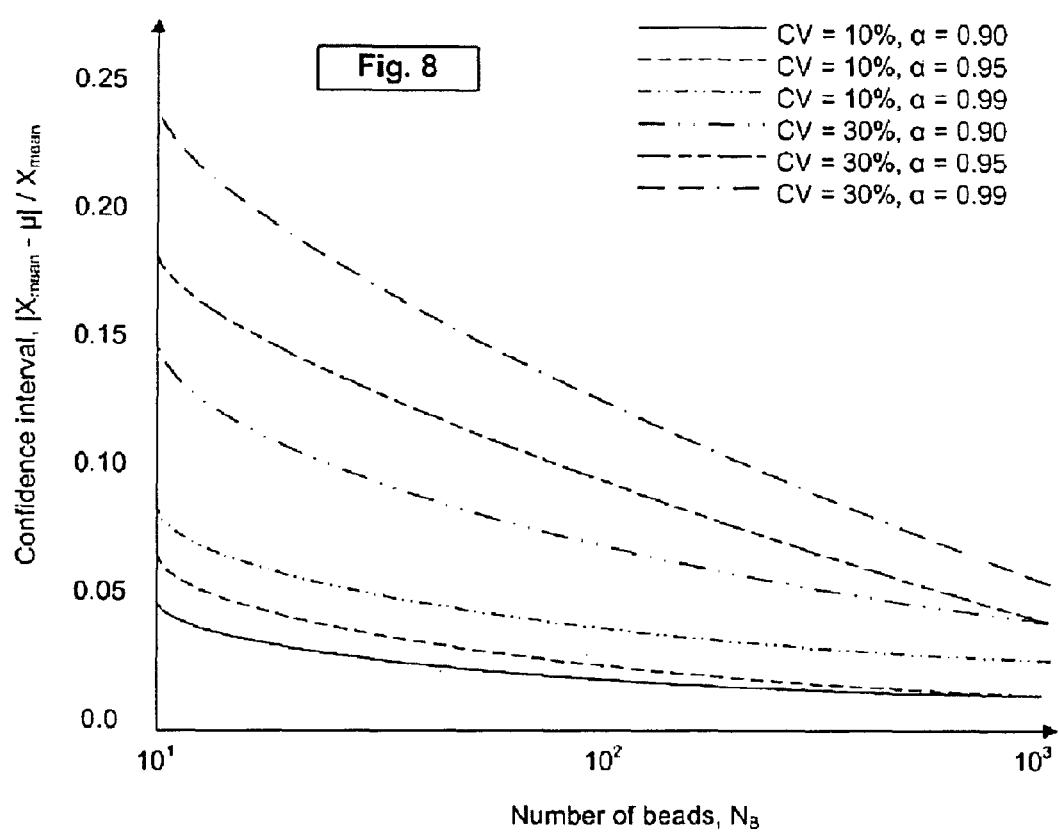

Fig. 9

Table 1

| Sample ID | Number of Shine Beads (With Assay Signals) | | | | Predicted Antibodies |
|---|---|---|---|---|---|
| | P6-Coupled Beads | P8-Coupled Beads | P12-Coupled Beads | total | |
| 1 | | | | 0 | negative sample |
| 2 | 50 | | | 50 | anti-P6 (+) |
| 3 | | 100 | | 100 | anti-P8 (+) |
| 4 | | | 200 | 200 | anti-P12 (+) |
| 5 | 50 | 100 | | 150 | anti-P6 & P8 (+) |
| 6 | 50 | | 200 | 250 | anti-P6 & P12 (+) |
| 7 | | 100 | 200 | 300 | anti-P8 & P12 (+) |
| 8 | 50 | 100 | 200 | 350 | anti-P6, P8, & P12 (+) |

Fig. 10

Table 2

| Bead Type | Peptide ID | # of Parts | # of Beads |
|---|---|---|---|
| A | P1,P5 | 1 | 30 |
| A | P1,P6 | 3 | 90 |
| A | P1,P7 | 6 | 180 |
| A | P1,P8 | 10 | 300 |
| B | P2,P5 | 3 | 90 |
| B | P2,P6 | 6 | 180 |
| B | P2,P7 | 10 | 300 |
| B | P2,P8 | 1 | 30 |
| C | P3,P5 | 6 | 180 |
| C | P3,P6 | 10 | 300 |
| C | P3,P7 | 1 | 30 |
| C | P3,P8 | 3 | 90 |
| D | P4,P5 | 10 | 300 |
| D | P4,P6 | 1 | 30 |
| D | P4,P7 | 3 | 90 |
| D | P4,P8 | 6 | 180 |

Fig. 11

Table 3A

| Sample ID | Number of Shine Beads (sub-total) | | | | Predicted Antibodies |
|---|---|---|---|---|---|
| | A | B | C | D | |
| 1 | 600 | 0 | 0 | 0 | P1(+) |
| 2 | 0 | 600 | 0 | 0 | P2(+) |
| 3 | 0 | 0 | 600 | 0 | P3(+) |
| 4 | 0 | 0 | 0 | 600 | P4(+) |
| 5 | 30 | 90 | 180 | 300 | P5(+) |
| 6 | 90 | 180 | 300 | 30 | P6(+) |
| 7 | 180 | 300 | 30 | 90 | P7(+) |
| 8 | 300 | 30 | 90 | 180 | P8(+) |
| 9 | 600 | 90 | 180 | 300 | P1(+),P5(+) |
| 10 | 600 | 180 | 300 | 30 | P1(+),P6(+) |
| 11 | 600 | 300 | 30 | 90 | P1(+),P7(+) |
| 12 | 600 | 30 | 90 | 180 | P1(+),P8(+) |
| 13 | 120 | 270 | 480 | 330 | P5(+),P6(+) |
| 14 | 210 | 390 | 210 | 390 | P5(+),P7(+) |
| 15 | 330 | 120 | 270 | 480 | P5(+),P8(+) |
| 16 | 270 | 480 | 330 | 120 | P6(+),P7(+) |
| 17 | 390 | 210 | 390 | 210 | P6(+),P8(+) |
| 18 | 480 | 330 | 120 | 270 | P7(+),P8(+) |

Fig. 12

Table 3B

| Sample ID | Peptide ID/ # of Bead With Signals/Type A |  |  |  |  | Peptide ID/ # of Bead With Signals/Type B |  |  |  |  |
|---|---|---|---|---|---|---|---|---|---|---|
|  | P1,P5 | P1,P6 | P1,P7 | P1,P8 | A-Total | P2,P5 | P2,P6 | P2,P7 | P2,P8 | B-Total |
| 1 | 30 | 90 | 180 | 300 | 600 | 0 | 0 | 0 | 0 | 0 |
| 2 | 0 | 0 | 0 | 0 | 0 | 90 | 180 | 300 | 30 | 600 |
| 3 | 0 | 0 | 0 | 0 | 0 | 0 | 0 | 0 | 0 | 0 |
| 4 | 0 | 0 | 0 | 0 | 0 | 0 | 0 | 0 | 0 | 0 |
| 5 | 30 | 0 | 0 | 0 | 30 | 90 | 0 | 0 | 0 | 90 |
| 6 | 0 | 90 | 0 | 0 | 90 | 0 | 180 | 0 | 0 | 180 |
| 7 | 0 | 0 | 180 | 0 | 180 | 0 | 0 | 300 | 0 | 300 |
| 8 | 0 | 0 | 0 | 300 | 300 | 0 | 0 | 0 | 30 | 30 |
| 9 | 30 | 90 | 180 | 300 | 600 | 90 | 0 | 0 | 0 | 90 |
| 10 | 30 | 90 | 180 | 300 | 600 | 0 | 180 | 0 | 0 | 180 |
| 11 | 30 | 90 | 180 | 300 | 600 | 0 | 0 | 300 | 0 | 300 |
| 12 | 30 | 90 | 0 | 0 | 120 | 0 | 0 | 0 | 30 | 30 |
| 13 | 30 | 0 | 180 | 0 | 210 | 90 | 180 | 0 | 0 | 270 |
| 14 | 30 | 90 | 0 | 300 | 330 | 90 | 0 | 300 | 0 | 390 |
| 15 | 30 | 0 | 180 | 0 | 270 | 90 | 0 | 0 | 30 | 120 |
| 16 | 0 | 90 | 0 | 300 | 390 | 0 | 180 | 300 | 0 | 480 |
| 17 | 0 | 90 | 0 | 0 | 480 | 0 | 180 | 0 | 30 | 210 |
| 18 | 0 | 0 | 180 | 300 | 480 | 0 | 0 | 300 | 30 | 330 |

Fig. 13

Table 3C

| Sample ID | Peptide ID/ # of Bead With Signals/Type C | | | | | | Peptide ID/ # of Bead With Signals/Type D | | | | | |
|---|---|---|---|---|---|---|---|---|---|---|---|---|
| | P3,P5 | P3,P6 | P3,P7 | P3,P8 | C-Total | | P4,P5 | P4,P6 | P4,P7 | P4,P8 | D-Total | |
| 1 | 0 | 0 | 0 | 0 | 0 | | 0 | 0 | 0 | 0 | 0 | |
| 2 | 0 | 0 | 0 | 0 | 0 | | 0 | 0 | 0 | 0 | 0 | |
| 3 | 180 | 300 | 30 | 90 | 600 | | 0 | 0 | 0 | 0 | 0 | |
| 4 | 0 | 0 | 0 | 0 | 0 | | 300 | 30 | 90 | 180 | 600 | |
| 5 | 180 | 0 | 0 | 0 | 180 | | 300 | 0 | 0 | 0 | 300 | |
| 6 | 0 | 300 | 0 | 0 | 300 | | 0 | 30 | 0 | 0 | 30 | |
| 7 | 0 | 0 | 30 | 0 | 30 | | 0 | 0 | 90 | 0 | 90 | |
| 8 | 0 | 0 | 0 | 90 | 90 | | 0 | 0 | 0 | 180 | 180 | |
| 9 | 180 | 0 | 0 | 0 | 180 | | 300 | 0 | 0 | 0 | 300 | |
| 10 | 0 | 300 | 0 | 0 | 300 | | 0 | 30 | 0 | 0 | 30 | |
| 11 | 0 | 0 | 30 | 0 | 30 | | 0 | 0 | 90 | 0 | 90 | |
| 12 | 0 | 0 | 0 | 90 | 90 | | 0 | 0 | 0 | 180 | 180 | |
| 13 | 180 | 300 | 0 | 0 | 480 | | 300 | 30 | 0 | 0 | 330 | |
| 14 | 180 | 0 | 30 | 0 | 210 | | 300 | 0 | 90 | 0 | 390 | |
| 15 | 180 | 0 | 0 | 90 | 270 | | 300 | 0 | 0 | 180 | 480 | |
| 16 | 0 | 300 | 30 | 0 | 330 | | 0 | 30 | 90 | 0 | 120 | |
| 17 | 0 | 300 | 0 | 90 | 390 | | 0 | 30 | 0 | 180 | 210 | |
| 18 | 0 | 0 | 30 | 90 | 120 | | 0 | 0 | 90 | 180 | 270 | |

SEQUENCE LISTING

<160> NUMBER OF SEQ ID NOS: 4

<210> SEQ ID NO 1
<211> LENGTH: 24
<212> TYPE: DNA
<213> ORGANISM: Artificial Sequence
<220> FEATURE:
<223> OTHER INFORMATION: Artificial Probe

<400> SEQUENCE: 1

```
ggcaccatta aagaaaatat catc                                          24

<210> SEQ ID NO 2
<211> LENGTH: 24
<212> TYPE: DNA
<213> ORGANISM: Artificial Sequence
<220> FEATURE:
<223> OTHER INFORMATION: Artificial Probe

<400> SEQUENCE: 2
ggcaccatta aagaaaatat catt                                          24

<210> SEQ ID NO 3
<211> LENGTH: 40
<212> TYPE: DNA
<213> ORGANISM: Artificial Sequence
<220> FEATURE:
<223> OTHER INFORMATION: Artificial Primer

<400> SEQUENCE: 3
ggcgtcccaa aagggtcagt gagccttcag agggtaaaat                         40

<210> SEQ ID NO 4
<211> LENGTH: 40
<212> TYPE: DNA
<213> ORGANISM: Artificial Sequence
<220> FEATURE:
<223> OTHER INFORMATION: Artificial Primer

<400> SEQUENCE: 4
gcggtcccaa aagggtcagt cagtagctta cccatagagg                         40
```

NUMBER CODING FOR IDENTIFICATION OF SUBTYPES OF CODED TYPES OF SOLID PHASE CARRIERS

RELATED APPLICATIONS

This application is a divisional of U.S. patent application Ser. No. 10/943,760, filed Sep. 17, 2004, which claims priority to U.S. Provisional Application No. 60/504,294, filed Sep. 18, 2003, the entire contents of each of which are incorporated herein by reference in their entireties.

FIELD OF THE INVENTION

The invention is in the field of encoded carriers for chemical entities.

BACKGROUND

Solid phase carriers for multiplexed analysis of multiple analytes, preferably are encoded using one of several available color coding methods (see U.S. Ser. No. 09/448,420, filed Nov. 23, 1999, entitled "Color-Encoding and In-Situ Interrogation of Matrix-Coupled Chemical Compounds"; U.S. Ser. No. 10/348,165, filed Jan. 21, 2003, entitled "Method of Controlling Solute Loading of Polymer Microparticles," U.S. Pat. No. 4,499,052 "Apparatus for Distinguishing Multiple Subpopulations of Cells) to produce spectrally distinguishable carriers; or using chemical tagging methods such as those commonly employed for encoding of combinatorial libraries to produce carriers distinguishable by way of decoding these tags by one of several methods known in the art (see, e.g., U.S. Pat. No. 6,503,759 "Complex Combinatorial Chemical Libraries Encoded with Tags"). In applications of interest, solid phase carriers are functionalized to display chemical entities such as nucleic acid probes or protein receptors, each such entity being uniquely associated with a code and defining a carrier type. Preferably, the molecular analysis of multiple analytes is performed in accordance with the Random Encoded Array Detection (READ™) format, as described in U.S. application Ser. No. 10/204,799, filed on Aug. 23, 2002, entitled "Multianalyte Molecular Analysis Using Application-Specific Random Particle Arrays" using microparticles ("beads") as the solid phase carriers.

A method of encoding by providing multiple instances ("multiplicities") of each distinguishable type of carrier within a set of N such types has been described in connection with a flow cytometric multiplexed immunoassay format (See U.S. Pat. No. 5,567,627—Lehnen). Although Lehnen states that larger numbers of analytes may be analyzed with this method, the examples relate to small numbers, N, of analytes, where N ranges from 2 to 4.

However, the molecular analysis of multiple analytes, and particularly the analysis of nucleic acid sequences, generally must accommodate numbers of analytes in the range of tens of analytes, or about $10 \leq N \leq 100$. An example is the multiplexed analysis of the 25 mutations in the cystic fibrosis transmembrane regulator gene designated by the American College of Medical Genetics (ACMG) for pan-ethnic carrier screening, requiring at least 25 pairs of probes to discriminate normal and variant alleles.

To ensure an unambiguous decoding, application of the method in Lehnen for use in a method of encoding carriers requires a unique decomposition of N into summands, $m_k$, such that no partial sum obtained by adding two or more summands can be obtained in any other way of combining summands, and no summand is itself the sum of two or more of the other summands. For example, if N=10 analytes are to be displayed on uniquely coded carriers, one might select ten prime numbers in an attempt to construct a unique set of multiplicities as required by Lehnen, e.g.: $m_1$=5, $m_2$=7, $m_3$=11, $m_4$=13, $m_5$=17, $m_6$=19, $m_7$=23, $m_8$=29, $m_9$=31, $m_{10}$=37, only to discover that this prescription fails, even for this value of N=10, given that $m_1+m_4=m_2+m_3$ and other non-unique combinations, which can be seen. Therefore, the task of constructing a unique decomposition for any N represents a problem to which Lehnen does not provide a solution.

Additional difficulties arise when consideration is given to practical requirements in assay design. For example, in typical quantitative assays which may produce, for each of several types of constituent probes, signal intensities varying over a wide range, the respective mean signal intensities generally will not be known a priori. Thus, even in the case of only two different types of carriers, when the standard deviation of the assay signal produced by the multiple instances of the first type of probe is comparable to the difference in mean signal intensities of first and second types of probes, codes will be corrupted, decoding will be compromised and assay scores will be indeterminate. Assay signal intensities have been observed to vary by 10% to 30% about the mean over a specific carrier type.

Additional practical requirements place further constraints on practical codes. Thus, each $m_k$ is bounded from below as a result of placing confidence intervals on assay scores. As described in greater detail below, this constraint, the random encoded array (READ™) format or equivalent assay formats, requires minimal multiplicities in the range of 30-50 to ensure desirable confidence intervals on assay determinations. Each $m_k$ also is bounded from above by the fact that the total number of carriers, M, readily accommodated in a practical assay format and thus typically in the range of ~100 to ~10,000, is finite, where $M=\Sigma_{(k=1)\ to\ (k=N)}\ m_k$, implying an upper limit for each of the $m_k$. Further, in practice, the number of carriers of any given type contained in aliquots of suspension of nominally equal volumes will display a statistical variation, requiring that values of individual multiplicities be selected so as to differ from one another by at least several standard deviations about each mean, and thus not be spaced too closely. The methods described in Lehnen, therefore, do not enable multianalyte molecular analysis and also are not practical or desirable as a means of carrier encoding.

However, when number coding ("N-coding") is augmented by an additional code—such as chemical coding and specifically color coding ("C-coding")—and when applied to represent a finite, known number of outcomes for each of a multiplicity of probe types included in a multiplexed analysis, it is practical and desirable. In a multiplexed analysis of molecular analytes, N-coding permits the representation of a finite number of known or anticipated assay scores or outcomes for each of a multiplicity of types of probes or receptors included in the analysis. N-coding thus can be used to discriminate nucleic acid alleles by N-coded subtypes of carriers, each subtype displaying a probe matched to one of the known or anticipated alleles; specifically, N-coding can be used to discriminate normal and variant alleles by pairs of probes, one of these complementary to the normal ("wildtype", W) allele and represented by a multiplicity $m_W$, the other complementary to the variant ("V") allele and represented by a multiplicity $m_V$, where $m_V \neq m_W$ but both alleles share one color code. N-coding also can be used to discriminate epitopes by N-coded subtypes of carriers, each subtype displaying a receptor capable of binding to one of the known or anticipated epitopes of a ligand of interest, all such epitopes or ligands sharing one color code.

SUMMARY OF THE INVENTION

Number coding of pairs ("doublets") or small sets ("multiplets") of solid phase carriers provides distinguishable subtypes of a given type of such carriers, where each carrier type is distinguishable on the basis of a C-code. Such number coding is useful for augmenting a coding system, such as a color code, and thereby effectively multiplying the number of "colors" (distinguishable sub-types). It can be applied advantageously, for example, in multiplexed nucleic acid or protein analysis.

In one embodiment, members of a pair of probes are encoded by N-coding of solid phase carriers of the same color, but each of several such different pairs of probes will be associated with a carrier type of a different color. This embodiment is useful, for example, in multiplexed mutation analysis, where a color code can be augmented (effectively doubled) by N-coding carriers displaying pairs of probes, where the pair members are complementary to, respectively, a wild-type and variant allele.

In another embodiment, sets of probes complementary, for example, to a polymorphic region and to each of the four possible bases at a designated polymorphic position within the region, are encoded by N-coding of solid phase carriers of the same color, and each of several such different sets of probes will be associated with a carrier type of a different color.

In yet another embodiment, where, for example, there are multiple epitopes associated with a particular antigen, or where one merely wishes to increase the available coding, proteins (peptides) representing epitopes can be associated with a solid phase carrier and used to screen biological samples for reactive proteins or antibodies. This may be used, for example, where pairs or small sets of epitopes are associated with a particular antigen. In such case, the C-coding can be augmented by N-coding of solid phase carriers of the same color, where such a carrier subset carries the pairs or set of proteins corresponding to such pairs or sets of epitopes, as applicable.

The solid phase carriers preferably are microparticles which are assembled into planar arrays of particles on a substrate for use in the Random Encoded Array Detection (READ™) format of analysis, as disclosed in Ser. No. 10/032,657, filed Dec. 28, 2001, entitled "Multianalyte Molecular Analysis Using Application-Specific Random Particle Arrays" (incorporated by reference).

The methods herein are particularly useful in applications requiring, for each analyte, the determination of one among only a finite number of possible assay scores. Specifically, N-coding of pairs of solid phase carriers is practical because only a small number of carrier subtypes, and in the case of mutation analysis only two carrier subtypes, need be distinguished, and a unique code is trivially available.

BRIEF DESCRIPTION OF THE DRAWINGS

FIG. 4 depicts a histogram showing the number of beads displaying a certain intensity as a function of intensity, for detection of the "V" and "W" alleles using different numbers of carriers displaying probes which bind to the V or the W alleles. In the preferred case, the histogram has two distinct, non-overlapping peaks.

FIG. 5 depicts a plot of results as show in FIG. 4, but for overlapping histogram peaks in this case.

FIG. 6 is a histogram representing the probability of selecting a given number of carriers ("beads") of particular types of 70 subtypes, based on the evaluation of 40 random encoded arrays of beads, where the anticipated number of beads of each type was about 60. A total of about 3,500 beads (of 70 types) are anticipated to be present in each of the 40 bead arrays, based on an average 90% occupation of available sites. For each type, the CV was calculated over the population of 40 arrays evaluated.

FIG. 7 is a histogram plot as in FIG. 6, but for another type of beads.

FIG. 8 is a plot of confidence interval against number of beads, at different CVs and significance levels ($\alpha$).

FIG. 9 is Table 1, showing results from three synthetic peptides P6, P8, and P12 affixed to the same colored microspheres in separate reactions.

FIG. 10 is Table 2, showing bead types with different peptide pairs associated with beads.

FIG. 11-13 are, respectively, Table 3A to 3C, showing beads reactive with different samples.

DETAILED DESCRIPTION

Figure 1A:
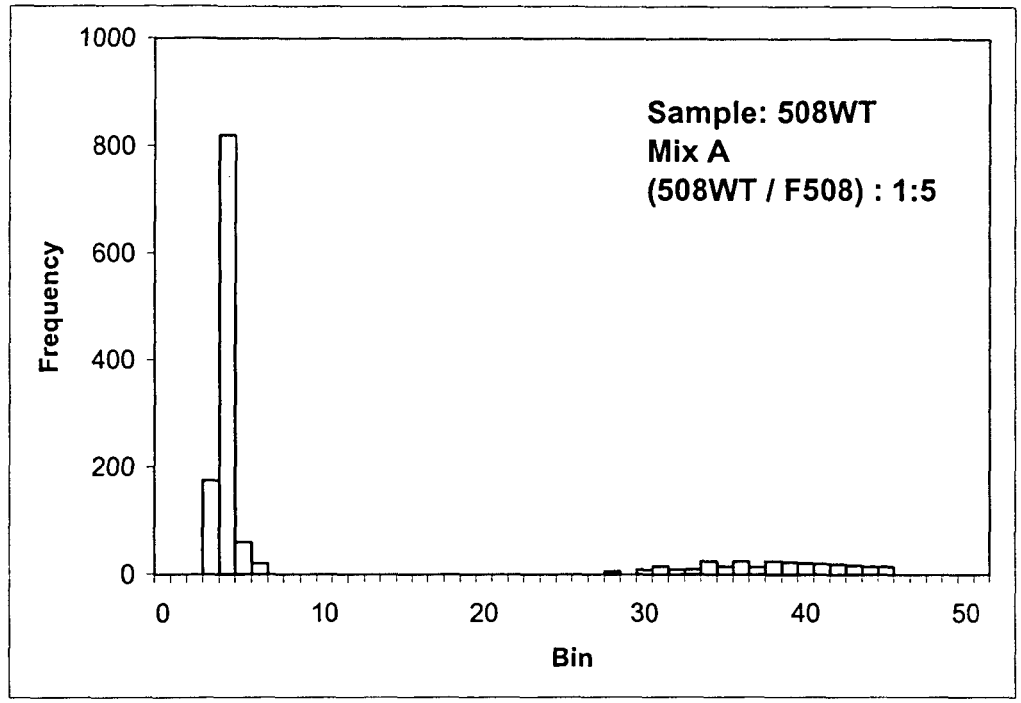
FIGS. 1A to 1D show assay results of numerical coding for detecting the F508 mutation using elongation detection, in the form of a series of four histograms, where, in each histogram, the number of beads displaying a signal of a certain intensity is plotted against intensity.

N-Coding of Pairs ("Doublets": Mutation Analysis and Carrier Screening—In the multiplexed analysis of mutations, a pair of probes is provided for each mutation of interest, a first probe designed to identify the "Wild-Type" ("W") and a second probe designed to identify the "Variant" ("V"). Identification may invoke hybridization (as disclosed in U.S. application Ser. No. 10/847,046, filed May 17, 2004 "Hybridization-Mediated Analysis of Polymorphisms (hMAP)," both being incorporated herein by reference) or elongation (as disclosed in U.S. application Ser. No. 10/271,602, filed Oct. 15, 2002 entitled "Multiplexed Analysis of Polymorphic Loci by Concurrent Interrogation and Enzyme-Mediated Detection," incorporated herein by reference).

For every type of C-coded carrier, a number $w:=n_C^W$, of carriers displaying the W-probe, and a number $v:=n_C^V$ (where $n_C^V \neq n_C^W$) of carriers displaying the V-probe are provided. $n_C^W$ and $n_C^V$ are selected so as to differ by a quantity $\Delta n_C$, which is sufficiently large to ensure that an unambiguous call can be made in view of the practical considerations and requirements discussed above. The selection criterion for $n_C^W$ and $n_C^V$ is discussed in greater detail below.

Each pair of probes can encounter only three possible scenarios: the W allele, the V allele or a heterozygous (H) target. The actual outcome is determined by "counting, comparing and (optionally) confirming" as follows:

```
Count the number of carriers, p := n_C+, (of, e.g., type C) which score
positive, as determined from the intensity of signal recorded after
completion of an assay designed to detect the presence of the W and/or
V form of the subsequence of interest; Count the number of carriers,
n := n_c-, (of type C) which score negative;
Compare:
   IF:
      p/w ~ 1:         THEN: W-allele;
      Confirm: n/v ~ 1;
   IF NOT, THEN IF
      p/v ~ 1:         THEN: V-allele;
      Confirm: n/w ~ 1;
   IF NOT, THEN IF
      p/(w+v) ~ 1:     THEN: H;
      Confirm: n/(w+v) ~ 0;
```

N-Coding of Multiplets: Polymorphisms and Antibody/Epitope Pairs

The N-coding system also could be used to detect single-nucleotide polymorphisms (SNPs). In such case, for example using eMAP™ detection, one would generate four different sets of probes, each complementary to the subsequence of interest but distinguished in that each different set would carry, at the 3' terminal probe position juxtaposed to the SNP site, one of four different nucleotides: A, C, G or T. Each set of probes would be attached to a carrier to form a carrier subtype, and there would be different numbers of each such subtype. The possible outcomes in such case would multiply to one positive for each of a possible four, or any combination of two positives for heterozygotes.

N-coding also could be used in assays for detecting the presence, in a sample, of antibodies capable of binding to peptides displayed on beads, or, in the reverse situation, for detecting peptides in a sample where the antibodies are displayed on beads. In such case, N-coding could be used for increasing the number of available codes, where, for example, color coding is used to discriminate among peptide-antibody combinations. That is, certain combinations can be encoded using carriers of the same color, by N-coding of such same-colored carriers to discriminate among such different combinations. An assay for detecting antibodies can be of particular utility for detecting auto-antibodies in a patient, in support of a diagnosis of autoimmune disease.

N-coding is useful when beads of a single color are employed, but are functionalized to display three different peptides to detect antibodies in a sample directed against one or more of the peptides, each peptide representing one specific epitope of the cognate antigen. Different numbers of beads displaying each of the three peptides would be pooled; i.e., X beads display peptide P1, Y beads display peptide P2, and Z display peptide P3. The pooled beads are then placed in contact with a sample which may contain antibodies against one or more of the peptides P1, P2 or P3. The sample is removed, and the beads are exposed to a labeled, secondary detection antibody which binds to any antibodies bound to the peptides on the beads (e.g., a goat anti-human antibody, if the sample is human); the assay signals are then recorded. The assay would have been first calibrated so that differences in relative signal can be correlated with numbers of labeled beads; i.e., one would be able to determine, based on the relative signal, whether X, Y, Z or a combination or subcombination of X, Y and Z beads generated a signal, indicating they had bound to antibodies in the sample. For example, the N-coding design in Table 2A may be used. Decoding the signal, therefore, indicates which specific epitope (or epitopes, if the signal indicates that a combination or subcombination of X, Y and Z beads generated a signal) were recognized by antibodies in the sample. This will permit classification of autoantibodies into subtypes for each autoantigen.

This assay system would be adequate where one was detecting relatively small numbers of different antibodies, and using numbers of beads where X, Y and Z are widely different. As noted above, N, the total number of beads, must have a unique decomposition, and the larger the numbers of peptides P1 . . . Px, the more difficult it is to construct such a unique decomposition.

Figure 3:
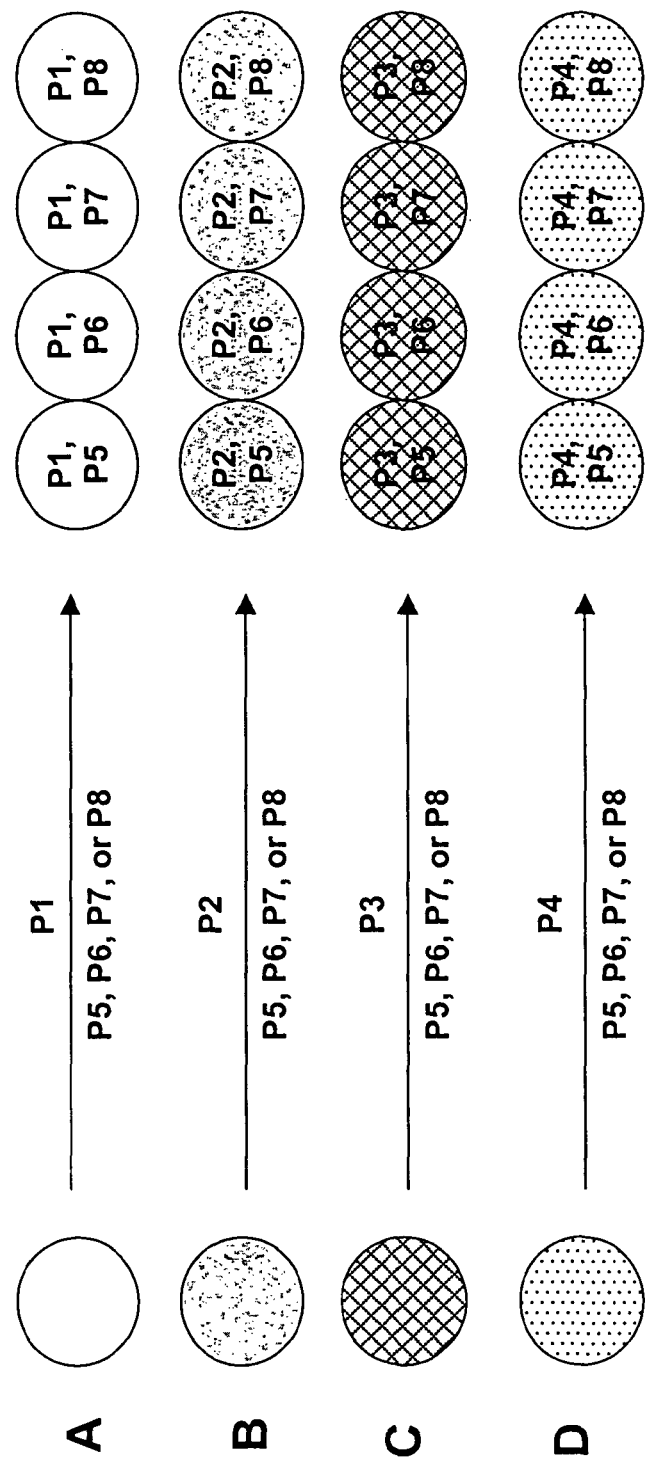
FIG. 3 depicts a coding system with four different C-codes ("colors") to encode bead types, for use in detecting antibodies against eight different peptides (P1 to P8).

This assay system could also be used where a population of beads has uniquely encoded (e.g., C-coded) populations, N-coding can be enhanced to distinguish among a number of particles exceeding the number of available C-codes. For example, as shown in FIG. 3, four C-coded bead populations are each associated with, respectively, proteins or peptides P1, P2, P3 and P4, and members of each bead type also are associated with proteins or peptides P5, P6, P7 and P8. It may be advantageous to have multiple peptides attached to beads in this manner, if one is mapping non-linear epitopes, as combinations of epitopes may, when attached to the beads, assume a configuration in which they react with antibodies, in the same manner as they do in vivo. As illustrated by the decompositions of binding shown in Tables 2 to and 3A to 3C (FIGS. 10-13), this encoding design can allow one to distinguish among antibodies directed to eight proteins or peptides, P1 to P8, or certain combinations thereof.

Number Coding under Uncertaint—Were carriers of each subtype identical, and experimental conditions perfect, then signals from each carrier of a given subtype would be identical, histograms of signal intensities recorded from instances of each subtype would contain δ-function peaks, and subtypes would be discriminated merely by ensuring, for the pair, $w := n_C^W \neq v := n_C^V$, or, for multiplets, a unique numerical decomposition. In practice, however, signals from nominally identical carriers display a finite variance, resulting, for example, from the chemical heterogeneity of carriers, statistical fluctuations in analyte capture to carrier-displayed probes and noise in signal acquisition. Under such conditions, exceptionally high signals recorded from nominally "negative" carriers may exceed exceptionally low signals recorded from nominally "positive" carriers, producing overlap of peaks for the W and V alleles in a histogram of intensities recorded from all carriers of a particular code, e.g., type C.

Confidence Intervals—A finite variance in assay signals recorded from carriers of different type will of course affect the reliability of discrimination between W and V alleles regardless of the method of coding. Thus, the standard methods of statistical analysis apply to the construction of confidence intervals—once the step of partitioning of the carrier population into types has been accomplished.

For example, if carriers for W and V probes were color coded, the construction of confidence intervals would proceed by the usual standard methods of statistical analysis, applied to intensities, $I_{W1}, I_{W2}, \ldots, I_{Ww}$ recorded from the w carriers displaying the W-probe and to intensities, $I_{V1}, I_{V2}, \ldots, I_{Vv}$ recorded from the v carriers displaying the V-probe. These sets of intensities yield mean values, Overline$\{I_W\}$ and Overline$\{I_V\}$, with the respective variances, $S_w^2$ and $S_v^2$. Under the assumption that the w and v intensities in the two sets represent independent observations, the t-distribution provides an expression relating the values (w, Overline$\{I_W\}$, $S_w^2$) and (v, Overline$\{I_V\}$, $S_v^2$) to the desired probabilities that confidence intervals constructed from the two sets of observations and placed on the mean values of the observed intensities contain the true mean values $<I_W>$ and $<I_V>$. Alternatively, the t-distribution can be applied in this circumstance to test whether the means of the two intensity populations are the same (or not) (see e.g, Chapt. 9 in "Principles of Statistics", M. G. Bulmer, Dover Publications, 1979, incorporated by reference).

The construction of a desired confidence interval to be placed on mean values requires a minimal number of observations, or here, a minimal number of carriers of each type, thereby setting a lower bound on w and v. Stated otherwise, decreasing the number of beads for a given CV and mean value increases the confidence interval.

FIG. 8 shows the confidence interval for cases where the assay CV is 10% and 30%. The interval defining the range of the calculated mean is plotted against the minimum number of beads $N_B$ necessary for significance levels of 90%, 95% and 99%. A larger number of beads ensures that the confidence interval is smaller.

Partitioning—In contrast to other encoding methods such as C-coding, N-coding is subject to additional uncertainty as a result of peak overlap and equivalent ambiguities affecting recorded assay signal intensities. Thus, referring to N-coding of pairs in the context of mutation analysis, partitioning into + and − subtypes may not be obvious by mere inspection of the data, as presumed in the Count-Compare-Confirm procedure of determining subtypes.

In such a circumstance, the partitioning step may be performed by introducing a suitable optimality criterion, assuming, for the moment, that $w:=n_C^W$ and $v:=n_C^V$ are known, for example, by explicit counting of carriers of each subtype prior to pooling. While described here for a pair of subtypes, the partitioning process is readily generalized to the discrimination of other than pairs by considering two or more thresholds in the partitioning step in accordance with the known instances for each possible subtype.

---

Construct a histogram of intensities recorded from all carriers sharing one C-code;
IF (histogram has only a single peak such that : n+/(w + v) ~ 1) THEN: H
ELSE find an optimal threshold, T, such that:
    $(n+(T) - w)^2 = \min$ AND $(n-(T) - v)^2 = \min$ THEN: W allele
OR
    $(n+(T) - v)^2 = \min$ AND $(n-(T) - w)^2 = \min$ THEN: V allele
wherein n+(T) and n−(T) are obtained by integration over the two partitions produced by partitioning of the histogram in accordance with the selection of the threshold T.

---

In the event of peak overlap, the experimentally recorded numbers $p:=n+(\tau)$ of "positive" intensities, $I_1^+, I_2^+, \ldots, I_p^+$ and $n:=n-(\tau)$ of "negative" $I_1^-, I_2^-, \ldots, I_n^-$, will depend on the threshold $\tau$. For example, exceptionally low signals recorded from nominally "positive" carriers may exceed exceptionally high signals recorded from nominally "negative" carriers, and once a threshold is selected, a certain number of "false negatives" and "false positives" will result. That is, carriers whose assay signal intensities fall into the peak overlap region may be assigned incorrect codes. The numbers p and n will then differ from the numbers w of particles displaying a probe matching the W-allele and v of particles displaying a probe matching the V-allele. Accordingly, to ensure robust N-coding, the choice of w and v must be such that peak overlap will not corrupt the code (FIG. 5).

A first condition ensuring robust N-coding may be based upon the observation that the maximal number, e, of errors in carrier type assignments will result when all errors either are false negatives, n→n+e, p→p−e, or false positives, n→n−e, p→p+e, and that this maximal number will be an increasing function of the magnitude of peak overlap, $\Sigma: e=e(\Sigma)$. That is, extreme values of the threshold, $\tau$, either to the right extreme of the overlap region or to the left extreme of the overlap region will produce the greatest deviations in n and p (FIG. 5).

Thus, a conservative criterion guiding the selection of w and v can be stated as follows:

---

| | |
|---|---|
| IF (without overlap: p > n) | THEN ensure p − e > n + e with overlap. |
| ELSE IF (without overlap: p < n) | THEN ensure p + e < n − e with overlap |

---

To ensure that these conditions are met, N-coding is preferably used only when it can be ensured that the N-coded subtypes produce substantially different assay signal intensities, thereby minimizing peak overlap.

That is, N-coding in accordance with the present invention preferably is used to represent discrete outcomes of an assay such that overlap between partitions in an intensity histogram is negligible. This is ensured by employing N-coding to represent assay outcomes only when the observed mean assay signal intensities are separated by at least one standard deviation, and preferably three standard deviations, to minimize the maximal number of possible false negatives or false positives. Alternatively, if a peak overlap of magnitude $\Sigma$ is anticipated, w and v must be chosen in accordance with a design criterion such as the one stated above.

Number Fluctuations—In addition to accounting for experimental uncertainty in the determination of the values of p and n, allowance also must be made for statistical uncertainty regarding the values w and v themselves. Such uncertainty can arise as a result of fluctuations in the number of particles contained in aliquots (of nominally identical volume) that are prepared in the course of practicing the invention.

For example, if, as in READ™, carriers are placed into a random array in a designated area of a planar substrate, fluctuations in the number of each carrier subtype included in the array are expected to be in accordance with a certain probability distribution whose mean is related to the concentration of the carrier reservoirs, preferably maintained in the form of a stable suspension, as described in Example 3.

Accordingly, actually realized values of w and v are determined only to within a certain range of possible values, namely $w^*=w\pm\delta w$ and $v^*=v\pm\delta v$, as shown by comparison of FIGS. 6 and 7, and allowance must be made for this uncertainty in the selection of the design values for w and v. For example, in the case of Poisson statistics, $\delta w \sim \langle w \rangle$, $\delta v \sim \langle v \rangle$, i.e., significant deviations of w and v are possible. Thus, a necessary condition to be satisfied by a robust N-code may be stated as follows:

---

IF (N-code is to ensure $v^* < w^*$) :
    THEN select v, w such that $v + \delta v < w − \delta w$
ELSE IF (N-code is to ensure $v^* > w^*$) :
    THEN select v, w such that $v − \delta v > w + \delta w$

---

In addition to this condition, a robust N-code also must take into account experimental uncertainties such as those discussed above which may affect the observed counts, p and n. Thus, a more general criterion guiding the selection of w and v can be stated as follows:

```
IF (N-code is to ensure ( |p–w*| < |p–v*| ) AND
    ( |n–v*| < |n–w*| )                                /* W allele */
        THEN ensure   max{ |p ±e – w*| } < min{ |p ± e – v*| } AND
                      max{ |n ±e – v*| } < min{ |n ± e – w*| }
ELSE IF (N-code is to ensure ( |p–v*| < |p–w*| ) AND
    ( |n–w*| < |n–v*| )                                /* V allele */
        THEN ensure   max{ |p ±e – v*| } < min{ |p ±e – w*| } AND
                      max{ |n ±e – w*| } < min{ |n±e – v*| }
```

These multiple conditions to be placed upon a proper choice of w and v for robust N-coding restrict the practical use of N-coding as a general encoding methodology, as discussed at the outset. N-coding is then particularly useful in connection with a color code ("C-code") because it reduces the set of color codes required for encoding of a given number of probes. For example, for the ACMG panel of 25 CF mutations requiring, instead of 50 color codes, only 25 color codes are required. Conversely, N-coding extends by a factor of two the coding complexity of a given set of color codes, thereby facilitating the process of manufacturing sets of color-encoded particles. Therefore, provided that N codes are constructed in accordance with the design rules outlined above, N coding can be used as part of a coding system involving color or other encoding markers, for certain of the carriers in a larger group, where such carriers are encoded identically but for their number codes.

EXAMPLES

Example 1

N-Coding of eMAP Probes for Detection of ΔF 508 CF Mutation

Mutation analysis was performed by placing members of a probe pair, designed to detect wild type and the ΔF 508 cystic fibrosis ("CF") mutation on beads of the same color, but selecting different numbers of V-beads and W-beads. Assay results were analyzed by recording signal intensities indicating hybridization of probe and target, and by analyzing these results in accordance with the histogram representation and CCC procedure described herein. Protocols—Wild type (W) and mutant (V) probes relating to the ΔF 508 CF mutation fixed to beads of the same color, and beads were pooled at different ratios of W to V probes and assembled into planar arrays in accordance with the READ™ format. On a first chip, the ratio of W:V was 1:5, and on a second chip the ratio of W:V was 5:1.

For detection of hybridization of probe and target, an elongation assay ("eMAP" see U.S. application Ser. No. 10/271,602, filed Oct. 15, 2002, incorporated by reference) was used. Known wild type and ΔF 508 heterozygous samples were applied to both types of chips, and histograms were generated. See FIGS. 1A to 1D.

Bead Functionalization:

Aliquots of a suspension of a bead designated G3H (a blue-green tosylated bead modified with Bovine Serum Albumin ("BSA") in accordance with the methods disclosed in a co-pending application was functionalized with each of the following amino-modified DNA probes:

508W:
                                            (SEQ ID NO. 1)
Sequence:    GGC ACC ATT AAA GAA AAT ATC ATC ΔF 508:
                                            (SEQ ID NO. 2)
Sequence:    GGC ACC ATT AAA GAA AAT ATC ATT The following protocol was used to attach these probes to the BSA-modified beads.

BSA Protocol:
1. Add 100 μL of beads to a tube containing 500 μL PBST, mix with vortex
2. Centrifuge for 1 min and remove the supernatant
3. Add 500 μL MES (0.1M, pH 4.5), mix with vortex,
4. Centrifuge for 1 min and remove supernatant
5. Prepare 0.05M of EDAC in MES right before use:
    a. Take EDAC out of freezer and let it warm to room temperature for 30 min
    b. Add 4 mL of MES (0.1M, pH 4.5) to 40 mg EDAC, mix with vortex
6. Add 500 μL of EDAC solution to each tube of beads
7. Add 10 μL probe (100 μM) to each bead suspension
8. Allow the beads to react for 1 hour at room temperature with end-over-end mixing
9. Add 100 μL of PBST to each tube after reaction, mix with vortex, centrifuge for 1 min, and remove supernatant
10. Wash beads twice with 500 μL of PBST and resuspend the beads in 100 μl, of TBS-2.

Bead Pooling:

Two pools were prepared using beads functionalized with 508W and ΔF 508 probes, as well as beads modified with OligoC (negative control) and probes matching beta-actin (positive control). In Pool A, the ratio of 508WT to F508 was 1:5, while in Pool B, the ratio was 5:1.

The following pooling protocol was used:
1. Add each of the four modified beads to an empty tube according to the volumes noted below
2. Wash beads once in 100 μL 10 mM Tris
3. Resuspend beads in 36 μl, 10 mM Tris Pool A:

| Bead | Volume added (μL) |
| --- | --- |
| G3H-508WT | 1 |
| G3H-F508 | 5 |
| G4B-OligoC-2 | 15 |
| G1E-BA | 15 |

Pool B:

| Bead | Volume added (μL) |
| --- | --- |
| G3H-508WT | 5 |
| G3H-F508 | 1 |
| G4B-OligoC-2 | 15 |
| G1E-BA | 15 |

Assembly of Random Encoded Bead Arrays:

A total of four arrays were assembled on the upper surface of a substrate (a "chip"), where two of these arrays were composed of Pool A, and the other two were composed of Pool B.

Elongation Assay:

For the elongation, 6.5 μL PCR product was extracted from known WT or M samples and placed into a PCR tube, to which 2 μL Exo-sap was added. The mixture was incubated at 37° C. for 25 min and 80° C. for 15 min (in a thermocycler). Thereafter, λ exonuclease was used for digestion into single stranded DNA. The reaction mixture included each of: dGTP, dTTP, dATP and dCTP. Following PCR amplification, the following Ex-10 primers were used in multiplexed PCR:

```
SEQ ID NO. 3:
GGC GTC CCA AAA GGG TCA GTG AGC CTT CAG AGG GTA
AAA T

SEQ ID NO. 4:
GCG GTC CCA AAA GGG TCA GTC AGT AGC TTA CCC ATA
GAG G
```

The results of the assay are shown in FIGS. 1A to 1D, in the form of a series of four histograms. In each histogram, the number of beads displaying a signal of a certain intensity is plotted against intensity. In FIG. 1A, a wild-type ("W") sample is added to a bead pool in which the ratio of the number of beads functionalized with probes complementary to the W subsequence to that of beads functionalized with probes complementary to the variant ("V") is 1 to 5. The histogram has two peaks, but, as expected, the peak corresponding to the beads producing a positive signal has only a small area, indicating that only a small number of beads produce a positive signal.

Figure 1B:
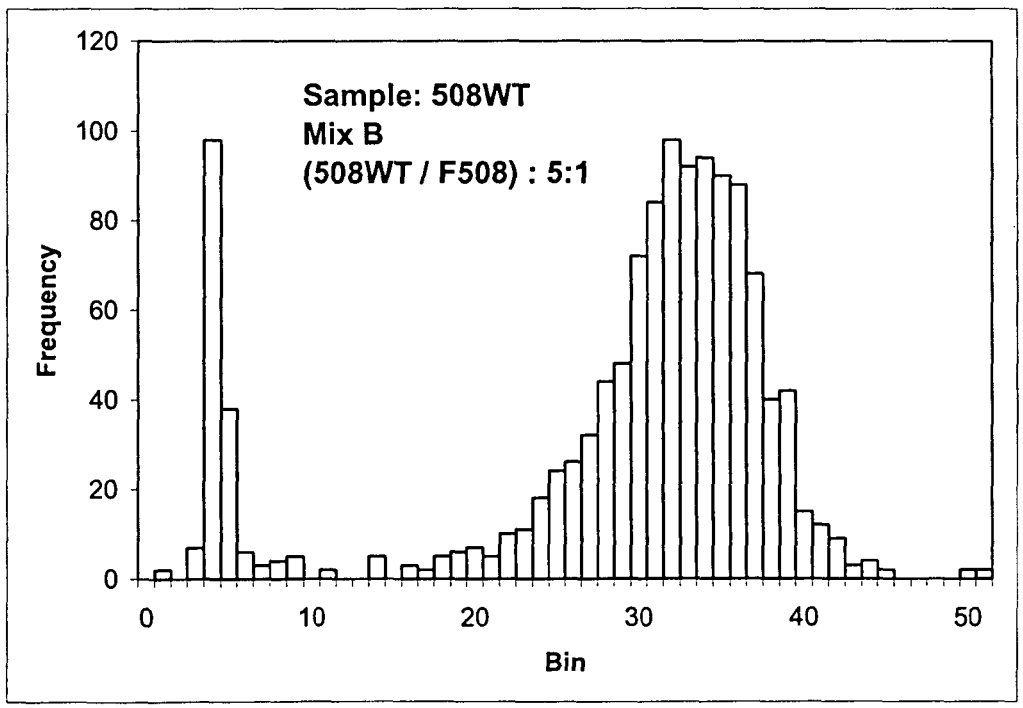
Figure 1C:
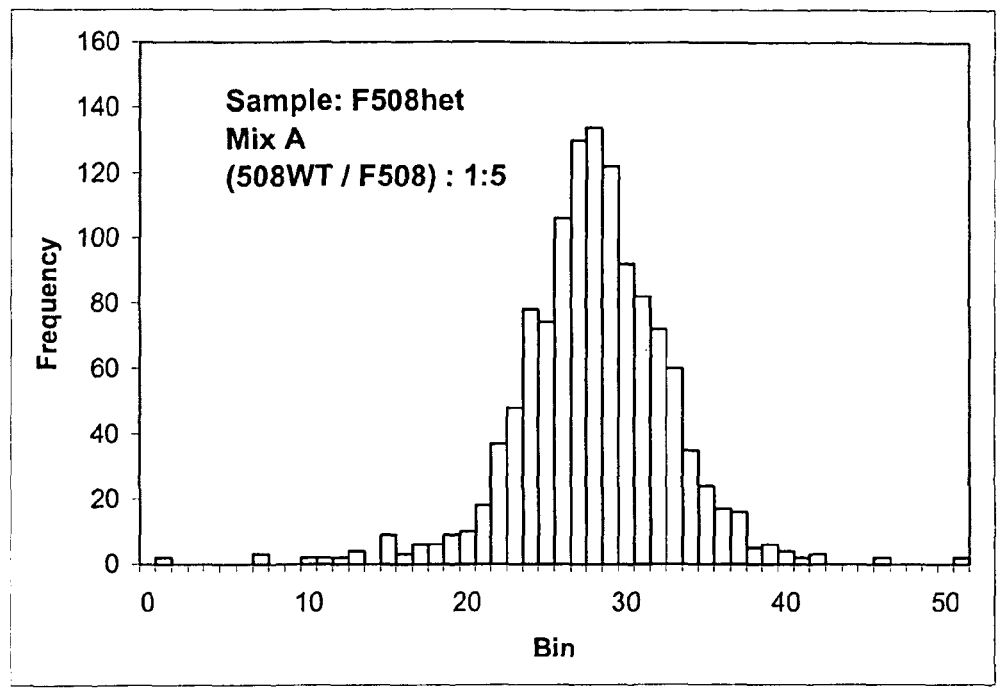
Figure 1D:
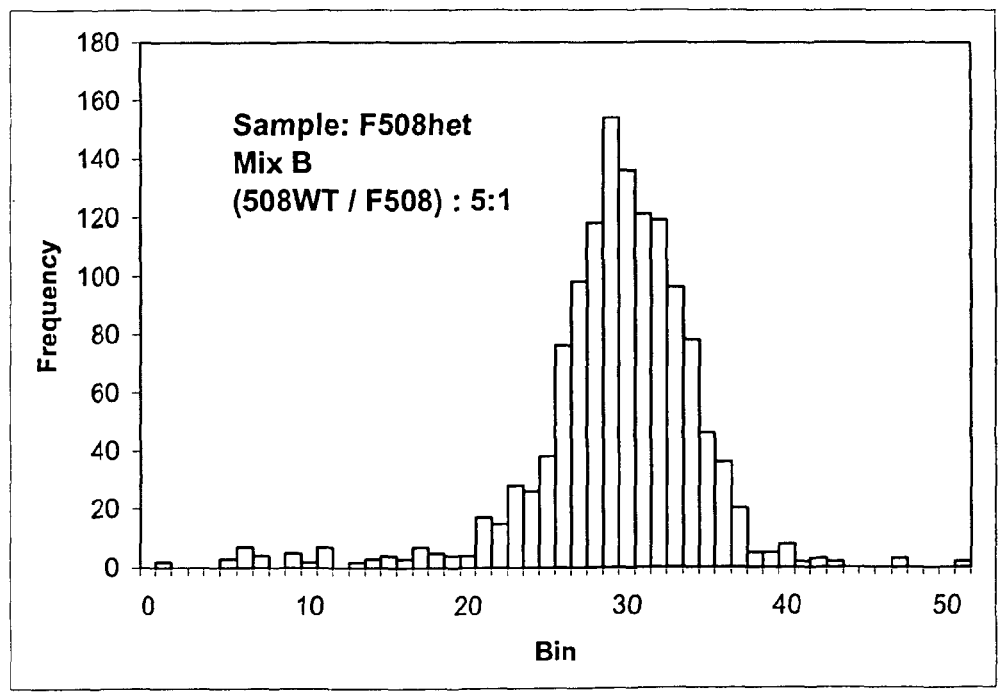
Figure 2:
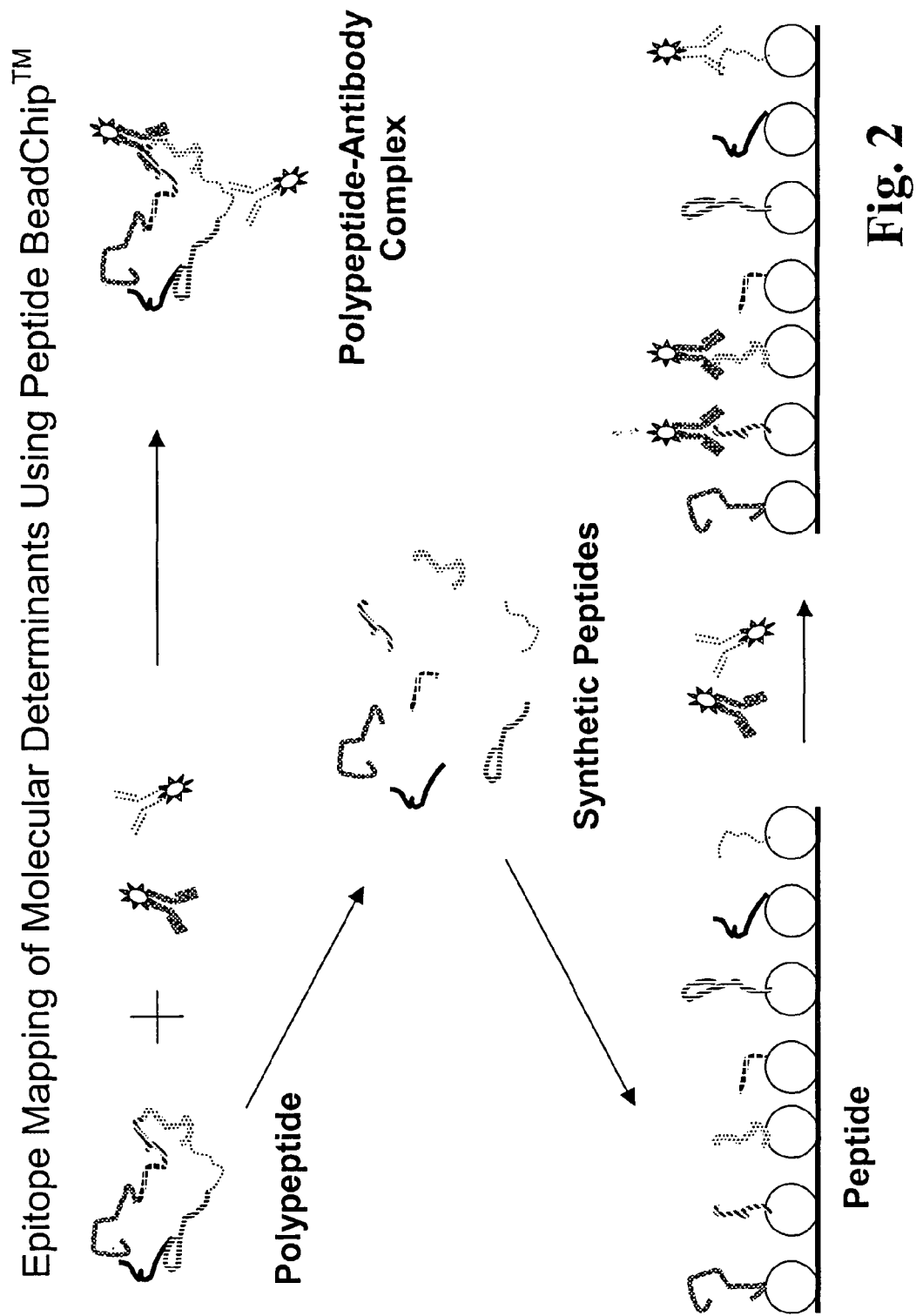
FIG. 2 depicts the native conformation of a protein which can be bound to either of two antibodies; the generation of synthetic peptide fragments corresponding to different linear epitopes of the protein and attaching the fragments to beads; and, the binding of labeled antibodies to the peptide fragments on the beads. A labeled secondary antibody could be used for detection, if the peptide fragments were initially bound by an unlabeled antibody (not shown).

In FIG. 1B, the sample is the same, but the ratio of beads of each type is reversed, and, as expected, the reverse ratio of peak areas is observed in the histogram. In FIGS. 1C and 1D, the sample is heterozygous for W and V, and, as expected, irrespective of the ratio of V and W, a large number of beads produce a positive signal.

Example 2

Detecting Auto-Antibodies

As shown in Table 1 (FIG. 9), three synthetic peptides P6, P8, and P12 are affixed to the same colored microspheres in separate reactions. These synthetic peptides are biotinylated at their N-termini with an 18-carbon spacer and immobilized by way of biotin-neutravidin complex formation. Beads are pooled, for example, at ratios of one part of P6-functionalized beads, two parts of P8-functionalized beads, and four parts of P12-functionalized beads and an array is assembled on the surface of a silicon chip (Beadchip™).

Beadchips were incubated in separate experiments with two 1:20 diluted serum samples positive for antibody directed against a lupus characteristic antigen, SCL-70 (#1764 from BiosPacific and #68933 from METIC Lab. After removing non-reacted antibodies, specific antibodies captured by the peptides were visualized using a fluorescently labeled goat-anti-human IgG antibody-conjugate. Decoding and assay images were acquired using a microscope equipped with a CCD camera, as in the previous example. The assay signals were extracted, and the Pi/P7 ratios (peptide-specific signal intensity vs. the signal intensity of negative control peptide, P7) were calculated. Beads with an intensity value significantly higher than that of the negative control were designated positive.

The presence of P6, P8 or P12-specific antibodies was determined by the relative numbers of positive beads. As shown in Table 1 (FIG. 9), assaying sample #1764 yielded 300 positive beads, meaning the positive beads captured anti-P8 (100 positive beads) and anti-P12 (200 positive beads) antibodies. Sample #68933 yielded 150 positive beads, meaning the positive beads captured anti-P6 (50 positive beads) and anti-P8 (100 positive beads) antibodies.

Example 3

Number Fluctuations in Random Encoded Bead Arrays

To prepare a pool of 50 types of encoded carriers in the form of polymer microparticles ("beads") of 3 μm diameter, 50 μl aliquots of each bead type are taken from a reservoir containing 1 ml of a stable suspension and split in order affix to each particle of a specific type a selected chemical entity such as an oligonucleotide probe. Next, 5 μl aliquots of probe-functionalized beads are taken from each reaction container and pooled to produce 250 μl of suspension containing 50 types of functionalized beads. Finally, in accordance with the Random Encoded Array Detection (READ) format, a 0.5 μl aliquot of pooled bead suspension is placed onto a planar silicon substrate, covering an area of approximately 1 mm$^2$ which includes a designated area of 300 μm by 300 μm, thus approximately 10% of the total area, for assembly of a planar array of 4000.

Under these assumptions about the relative size of aliquot ("sample") and reservoir, and about the relative size of designated area and total area of substrate, bead types will be distributed about the mean value, say the average density of particles in the original volume of suspension, in accordance with a Poisson distribution such as those shown in FIGS. 6 and 7.

The terms, expressions and examples hereinabove are exemplary only, and not limiting, and the invention is defined only in the claims which follow and includes all equivalents of the subject matter of the claims. Unless otherwise indicated, steps in method claims can be performed in any order, including but not limited to the order set forth in the claims.

What is claimed is:

1. A method of employing numerical encoding of particles in a bioassay, comprising:
providing uniquely color encoded groups of particles having ligands attached to said particles wherein each group of particles comprises two or more subtypes of particles having different ligands attached to said two or more subtypes of particles;
wherein the number of each subtype of particles provided has a unique decomposition into one or more summands, such that no partial sum of one or more summands can be obtained in any other way of combining summands, and no summand is itself the sum of two or more of the other summands;
conducting an assay by contacting the groups of particles with a sample comprising analytes;
determining, for each group of particles, the number of particles generating a positive assay signal, indicating reaction between a ligand and an analyte;
comparing, for each group of particles, said number of particles generating a positive assay signal with the number of particles of each subtype; and
determining, for each group of particles, the analytes present in the sample based on said comparing step.

2. The method of claim 1, wherein the different ligands attached to said two or more subtypes of particles comprise one of four oligonucleotide probes, each probe differing by having one of the nucleotides A, C, G or T in the 3' terminal position.

3. The method of claim 2 wherein a positive assay signal is generated by an elongation reaction.

4. A method of employing numerical coding of particles, comprising:
providing uniquely color encoded groups of particles having peptides or antibodies attached to said particles, wherein each group of particles comprises two or more subtypes of particles having different peptides or antibodies attached to said two or more subtypes of particles;
wherein the number of each subtype of particles provided has a
unique decomposition into one or more summands, such that no partial sum of one or more summands can be obtained in any other way of combining summands, and no summand is itself the sum of two or more of the other summands;
conducting an assay by contacting the groups of particles with a sample comprising analytes;
determining for each group of particles, the number of particles generating a positive assay signal, indicating reaction between a peptide or antibody and an analyte;
comparing for each group of particles, said number of particles generating a positive assay signal with the number of particles of each subtype; and
determining for each group of particles, the analytes present in the sample based on said comparing step.

5. The method of claim 4 wherein the ligands comprise peptides and the analytes comprise specific epitopes of auto-antibodies in the sample.

6. The method of claim 5, further comprising adding a secondary detection antibody which binds to auto-antibodies bound to the peptides.

7. The method of claim 4 wherein the color encoded groups comprise different colors corresponding to different groups of peptide ligands, each such group of peptides corresponding to epitopes of a specific autoantibody.

8. The method of claim 4 wherein two or more different types of peptides are attached to beads of the same group.

\* \* \* \* \*